US008258287B2

(12) United States Patent
Albina et al.

(10) Patent No.: US 8,258,287 B2
(45) Date of Patent: Sep. 4, 2012

(54) INTERFERING RNAS TARGETING THE MORBILLIVIRUS NUCLEOPROTEIN GENE

(75) Inventors: Emmanuel Albina, Prades-le-Lez (FR); Geneviève Libeau, Montpellier (FR); Djénéba Keita, Montpellier (FR); Renata Servan de Almeida, Prades-le-Lez (FR)

(73) Assignee: Centre de Cooperation Internationale en Recherche Agronomique pour le Developpment (CIRAD), Paris (FR)

( * ) Notice: Subject to any disclaimer, the term of this patent is extended or adjusted under 35 U.S.C. 154(b) by 388 days.

(21) Appl. No.: 12/158,620

(22) PCT Filed: Dec. 12, 2006

(86) PCT No.: PCT/FR2006/002819

§ 371 (c)(1), (2), (4) Date: Oct. 2, 2008

(87) PCT Pub. No.: WO2007/077339

PCT Pub. Date: Jul. 12, 2007

(65) Prior Publication Data

US 2009/0136544 A1 May 28, 2009

(30) Foreign Application Priority Data

Dec. 21, 2005 (FR) ..................................... 05 13029
Oct. 26, 2006 (FR) ..................................... 06 09400

(51) Int. Cl.
*C07H 21/02* (2006.01)
*C07H 21/04* (2006.01)
*C12Q 1/68* (2006.01)
*C12P 19/34* (2006.01)

(52) U.S. Cl. ....... 536/24.5; 435/6; 435/91.1; 435/91.31; 536/23.1; 536/24.32

(58) Field of Classification Search ........... 435/6, 91.31, 435/455, 91.1; 514/44; 536/23.1, 24.5, 24.32
See application file for complete search history.

(56) References Cited

U.S. PATENT DOCUMENTS 5,000,000 A * 3/1991 Ingram et al. ................ 435/161
6,165,786 A * 12/2000 Bennett et al. ............... 435/366
7,655,785 B1 * 2/2010 Bentwich ..................... 536/24.1
7,759,479 B1 * 7/2010 Dobie et al. ................. 536/24.5
2004/0265230 A1 * 12/2004 Martinez et al. ............. 424/1.49
2009/0028901 A1 * 1/2009 Palese et al. ............... 424/199.1

FOREIGN PATENT DOCUMENTS

WO WO 2004/045543 6/2004

OTHER PUBLICATIONS

Reynolds et al., Nature Biotech., vol. 22, No. 3, pp. 326-330 (2004).*
Crooke S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Reuter et al. "RNA interference with measles virus N, P, and L mRNAs efficiently prevents and with matrix protein mRNA enhances viral transcription." J. Virol. 80: 5951-5957, 2006.
Koschel et al. "Measels virus antisense sequences specifically cure cells persistently infected with measles virus." Virol. 207: 168-178, 1995.
STN Files: CA, CAPLUS, Registration No. 696718-24-8, 2004.
STN Files: CA, CAPLUS, Registration No. 722669-18-3, 2004.
STN Files: CA, CAPLUS, Registration No. 766411-19-2, 2004.
STN Files: CA, CAPLUS, Registration No. 797220-25-8, 2004.
STN Files: CA, CAPLUS, Registration No. 798072-85-2, 2004.
STN Files: CA, CAPLUS, Registration No. 808587-60-2, 2005.
STN Files: CA, CAPLUS, Registration No. 840612-28-4, 2005.
Schiffelers et al., "Cancer siRNA therapy by tumor selective delivery with ligand-targeted sterically stabilized nanoparticle," Nucleic Acids Research, 2004, 32(19): e149.
Zender et al., "Caspase 8 small interfering RNA prevents acute liver failure in mice," Proc. Natl. Acad. Sci. USA, 2003, 100(13): 7797-7802.
Bitko et al., "Inhibition of respiratory viruses by nasally administered siRNA," Nature Medicine, 2005, 11(1):50-55.

* cited by examiner

*Primary Examiner* — Jane Zara
(74) *Attorney, Agent, or Firm* — Morgan, Lewis & Bockius LLP

(57) ABSTRACT

The invention relates to interfering RNAs (siRNAs, shRNAs or pre-miRNAs) directed against conserved regions of the mRNA of the N gene encoding the morbillivirus nucleoprotein. The invention also relates to the use of said interfering RNAs for the production of medicaments for use in the treatment or prevention of a morbillivirus infection.

19 Claims, 6 Drawing Sheets

(a)

(b)

INTERFERING RNAS TARGETING THE MORBILLIVIRUS NUCLEOPROTEIN GENE

RELATED APPLICATIONS

Figure 1:

The present application is a U.S. National Phase Application of International Application PCT/FR2006/002816, filed Dec. 21, 2006, which claims the benefit of France Patent Applications 0513029, filed Dec. 21, 2005, and 0609400, filed Oct. 26, 2006, all of which are herein incorporated by reference in their entirety.

The present invention relates to the obtention of interfering RNAs capable of inhibiting the replication of morbillivirus, and to the use thereof for the prophylaxis or the treatment of morbillivirus infections, in particular for the obtention of vaccines.

The *Morbillivirus* genus belongs to the Paramyxoviridae family (Mononegavirales order) and includes in particular PPRV (small ruminant virus), RPV (Rinderpest virus or bovine plague virus), Mv (or MeV) (Measles virus), CDV (canine distemper virus or Carré's disease virus), DMV (dolphin morbillivirus) and PDV (phocine distemper virus).

The genome of the morbilliviruses is made up of a non-segmented, single-chain RNA, of negative polarity. Its structure is shown diagrammatically in FIG. 1. This single-chain RNA contains 6 genes: N, P, M, F, Hand L.

The products of the N (Nucleoprotein), P (Phosphoprotein) and L (Large protein, RNA polymerase dependent RNA) genes combine with the genomic viral RNA to form the nucleocapsid, which protects the viral genome, and constitutes a polymerase complex enabling the replication and transcription of the virus.

The products of the F (Fusion protein) and H (haemagglutinin) genes form part of the viral envelope. The H glycoprotein enables the attachment of the virus to the target cell, and the F glycoprotein is involved in the fusion of the viral envelope and the cell membrane.

The product of the M (Matrix protein) gene provides the interface between the nucleocapsid and the viral envelope.

RNA interference is a biological mechanism conserved in the course of evolution, which induces the specific extinction of genes by specific degradation of the messenger RNAs and or stoppage of the translation thereof. It was initially observed in *Caenorhabditis elegans*: injection of double-stranded RNA into this nematode inhibits the expression of the gene which contains the sequence of the molecule injected. It was then shown (Fire et al., Nature, 391, 806, 1998) that it was the double-stranded RNA which was responsible for this mechanism. In the cell, this double-stranded RNA is rapidly segmented by an endonuclease of the RNAase III type, named DICER, into small RNA of 21 to 28 nucleotides: the "small interfering RNA" siRNA (Zamore et al., Cell, 101, 25, 2000). The siRNAs are incorporated into an enzyme complex named RISC, for "RNA-Induced Silencing Complex". The RISC complex dissociates the strands of the siRNAs, and guides the pairing of the antisense strands with their complementary target sequences. The messenger RNAs containing these target sequences are then cleaved at the level of the duplex thus formed or their translation by the ribosomes is blocked.

In mammals, the presence of double-stranded RNA of size greater than 30 bp in a cell also induces a response mediated by interferon, which takes the form of a non-sequence specific degradation of the messenger RNAs. It has been shown (Elbashir et al., Nature, 411, 494, 2001) that the use of siRNAs in the cells of mammals did not induce this interferon type response, and made it possible specifically to inhibit the expression of genes containing the complementary sequences of these siRNAs.

The RNA interference has been widely used against viruses of various families, to target different genes with the aim of studying their function and/or for antiviral therapy purposes.

As regards the single-chain, negative, non-segmented RNA viruses, the first experiments were carried out in a pneumovirus, respiratory syncitial virus (RSV) (Bitko & Barik, BMC Microbiol, 1, 34, 2001). A siRNA targeting the gene for the P protein (subunit of RNA-dependent RNA polymerase), made it possible to obtain a 90% reduction in the expression of this protein, accompanied by a drastic diminution in the expression of all the viral proteins, and a reduction in the viral titer; a siRNA targeting the gene for the F protein induces a specific reduction in the synthesis of this protein, without affecting that of the other viral proteins, and inhibits the formation of syncitia.

The patent application PCT WO2005/056021 describes the use of a siRNA to target and inactivate the gene coding for a non-structural protein of RSV, the protein N Si, and thus increase the interferon response against RSV.

A recent publication by S. Barik (Barik, Virus Res, 102, 27, 2004) reviews the different approaches used to control the replication of single-chain, negative, non-segmented RNA by means of siRNA. The targeting of the genes coding for the P or L proteins, which are essential subunits of the viral polymerase complex, results in almost total disappearance of the synthesis of the viral RNA; the targeting of genes not essential to the synthesis of the viral RNA, but involved in the interactions of the virus with the host cell, produces more variable results.

RNA interference potentially represents a particularly interesting tool for the prophylaxis and/or the treatment of viral infections.

However, in spite of all the theoretical interest of this approach, its practical application to obtain effective antiviral activity poses different problems, relating in particular to the choice of the target sequences used in the siRNAs.

Here, the term "target gene" is used to designate a gene the extinction whereof it is desired to effect, and the term "target sequence" to designate a portion of the mRNA of a target gene recognized by a particular siRNA.

One of the problems relating to the choice of target sequences derives from the frequency of mutations, which is generally very high in viruses. A mutation occurring in the target sequence of a siRNA may allow the mutant virus to escape recognition. It is therefore desirable to choose a target sequence conserved between different viruses, where mutations are less liable to appear.

On the other hand, even if it is relatively easy, for a given target gene, to define siRNAs making it possible to obtain a certain attenuation of the expression of that gene, it is much more of a problem to obtain siRNAs making it possible to reach a level of extinction of the target gene sufficient to inhibit the viral replication.

It is in fact known that the efficacy of RNA interference can vary considerably from one siRNA to another. A very large number of factors appear to be involved in this variability, relating in particular to the target sequence itself (for example the G/C content, and the presence of certain bases at certain positions), to the position of that target sequence in the targeted gene, and to the presence of secondary structures of the mRNA capable of diminishing the accessibility of the target sequence for the siRNA. Different methods have been proposed for attempting to predict the efficacy of siRNAs (Gilmore et al., J Drug Target, 12, 315, 2004; Ui-Tei & Saigo, Tanpakushitsu Kakusan Koso, 49, 2662, 2004; Amarzguioui & Prydz, Biochem Biophys Res Commun, 316, 1050, 2004; Heale et al., Nucleic Acids Res, 33, e30, 2005; Reynolds et al., Nat Biotechnol, 22, 326, 2004; Arziman et al., Nucleic Acids Res, 33, W582, 2005; Huesken et al., Nat Biotechnol, 23, 995, 2005).

However, in spite of the progress made in the rationalization of the criteria for selection of optimal target sequences, this selection remains to a large extent empirical, and its results uncertain.

The inventors put forward the hypothesis that the extinction of the gene coding for the N protein of the morbilliviruses could make it possible to obtain the inhibition of viral replication, and undertook to study whether this extinction could be obtained by means of siRNAs targeting regions of this gene conserved between the morbilliviruses.

They succeeded in defining, in these conserved regions, loci containing target sequences making it possible to define siRNAs capable of inhibiting the expression of the N protein, this inhibition inducing inhibition of the replication of the morbilliviruses.

In the sense of the present invention, inhibition of the expression of a gene is understood to mean a diminution of at least 85%, preferably at least 90%, of the level of expression of a gene relative to its normal level. Inhibition of viral replication is understood to mean a diminution of at least 95%, preferably at least 98% in the quantity of virus relative to that produced under normal replication conditions.

Consequently, the subject matter of the present invention is a process for inhibiting the replication of a morbillivirus, characterized in that it comprises the inhibition of the N gene of a morbillivirus, by means of an interfering RNA targeting the region of the mRNA of said gene containing a motif including the following general sequence:

```
VRWYNNRNUGGUUNGRRA,          (SEQ ID No.: 1)
```

In particular, said motif can be defined by one of the following general sequences:

```
RRWYNNRHUGGUUHGARA or        (SEQ ID No.: 2)

VVRWYNNRNUGGUUNGRRA          (SEQ ID No.: 3)
```

The general sequences mentioned in the context of the exposition of the present invention were established from the alignment of sequences of N genes of the morbilliviruses PPRV, RPV, MV, CDV, DMV and PDV.

These sequences are shown in accordance with the IUPAC code, namely: A=adenine; C=cytosine; G=guanine; U=uracil; K=G or U; M=A or C; R=A or G; S=G or C; Y=C or U; W=A or U; B=G, U or C; D=G, A or U; H=A or C or U; V=G, A or C; N=A or C or G or U.

For example, to inhibit the expression of the N gene of the measles virus, an interfering RNA targeting the region of the mRNA of said gene containing the following sequence: GGUUCGGAUGGUUCGAGA (SEQ ID No.: 4) can be selected; to inhibit the expression of the N gene of RPV, an interfering RNA targeting the region of the mRNA of said gene containing the following sequence: AGUCUUACUGGUUGAGA (SEQ ID No.: 5) can be selected; to inhibit the expression of the N gene of PPRV, an interfering RNA targeting the region of the mRNA of said gene containing the following sequence: GGAUCAACUGGUUUGAGA (SEQ ID No.: 6) can be selected; to inhibit the expression of the N gene of CDV, an interfering RNA targeting the region of the mRNA of said gene containing the following sequence: AAUUAGGCUGGCUUAGAGA (SEQ ID No.: 7) can be selected; to inhibit the expression of the N gene of PDV, an interfering RNA targeting the region of the mRNA of said gene containing the following sequence: AAAUGGGCUGGUUAGAAA (SEQ ID No.: 8) can be selected; and to inhibit the expression of the N gene of DMV, an interfering RNA targeting the region of the mRNA of said gene containing the following sequence: GAACCCAUUGGIUUGAGA (SEQ ID No.: 9) can be selected.

Typically, said interfering RNA comprises a 19 to 29 bp, preferably 19 to 23 bp, portion of an antisense sequence of the N gene of a morbillivirus, said portion containing an antisense sequence of one of the target sequences defined here.

Thus, an interfering RNA targeting the region of the mRNA of the N gene comprising the sequence SEQ ID No.: 1 will comprise a motif defined by the general sequence UYCNAACCANYNNRWYB (SEQ ID No.: 10). If said interfering RNA more particularly targets the region of the mRNA of the N gene defined by the sequence SEQ ID No.: 2, it will comprise a motif defined by the general sequence UYUCDAACCADYNNRWYY (SEQ ID NO.: 11); and if it more particularly targets the region of the mRNA of the N gene defined by the sequence SEQ ID No.: 3, it will comprise a motif defined by the general sequence UYYCNAACCANYNNRWYBB (SEQ ID No.: 12).

As examples, to target the region of the mRNA of the N gene comprising the sequence SEQ ID No.: 1, it is possible to select:

- in the case of the measles virus, an interfering RNA which contains the following sequence: UCUCGAACCAUCCGAACC (SEQ ID No.: 13);
- in the case of RPV, an interfering RNA which contains the following sequence: UCUCAAACCAGUAAGACU (SEQ ID No.: 14);
- in the case of PPRV, an interfering RNA which contains the following sequence: UCUCAAACCAGUUGAUCC (SEQ ID No.: 15);
- in the case of CDV, an interfering RNA which contains the following sequence: UCUCUAACCAGCCUAAUU (SEQ ID No.: 16);
- in the case of PDV, an interfering RNA which contains the following sequence: UUUCUAACCAGCCCAUUU (SEQ ID No.: 17); and
- in the case of DMV, an interfering RNA which contains the following sequence: UCUCAAACCAAUGGGUUC (SEQ ID No.: 18).

According to the invention, to inhibit the replication of a morbillivirus, it is also possible to inhibit the N gene of said morbillivirus by means of interfering RNAs targeting other conserved regions of the mRNA of said gene, namely:

- an interfering RNA directed against the region of the mRNA of the N gene containing a motif defined by the following general sequence: GNMKRUUYWUGGUNKCNYU (SEQ ID No.: 19), and advantageously by the following general sequence: GSMGRUUYAUGGUVKCDYU (SEQ ID No.: 20).
- an interfering RNA directed against the region of the mRNA of the N gene containing a motif comprising the following general sequence: CHYUNGSNYUDCAYGARU (SEQ ID No.: 21), in particular a motif defined by the following general sequence: CHYUNGSNYUDCAYGARUU (SEQ ID No.: 22), or a motif defined by the following general sequence: GCHYUNGSNYUDCAYGARU (SEQ ID No.: 23).

Advantageously, said motif is defined by the following general sequence: GCHYUDGGNYUDCAYGARU (SEQ ID No.: 24).

As examples:

to inhibit the expression of the N gene of the measles virus, an interfering RNA targeting the region of the mRNA of said gene containing the following sequence: GCCGAUUCAUGGUCGCUCU (SEQ ID No.: 25), or an interfering RNA targeting the region of the mRNA of said gene containing the following sequence: GCUCUUGGACUGCAUGAAU (SEQ ID No.: 26) can be used;

to inhibit the expression of the N gene of RPV: an interfering RNA targeting the region of the mRNA of said gene containing the following sequence: GCAGAUUUAUGGUGGCAUU (SEQ ID No.: 27), or an interfering RNA targeting the region of the mRNA of said gene containing the following sequence: GCACUGGGCCUGCAUGAAU (SEQ ID No.: 28) can be used;

to inhibit the expression of the N gene of PPRV: an interfering RNA targeting the region of the mRNA of said gene containing the following sequence: GGCGGLUTCAUGGUAUCUCU (SEQ ID No.: 29), or an interfering RNA targeting the region of the mRNA of said gene containing the following sequence: GCAUUAGGCCUUCACGAGU (SEQ ID No.: 30) can be used;

to inhibit the expression of the N gene of CDV: an interfering RNA targeting the region of the mRNA of said gene containing the following sequence: GGCGAUUCAUGGUGGCGCU (SEQ ID No.: 31) and/or an interfering RNA targeting the region of the mRNA of said gene containing the following sequence: GCUCUUGGGUUGCAUGAGU (SEQ ID No.: 32) can be used;

to inhibit the expression of the N gene of PDV: an interfering RNA targeting the region of the mRNA of said gene containing the following sequence: GGCGAUUUAUGGUGGCAUU (SEQ ID No.: 33), or an interfering RNA targeting the region of the mRNA of said gene containing the following sequence: GCACUGGUCUACAUGAGU (SEQ ID No.: 34) can be used; and to inhibit the expression of the N gene of DMV: an interfering RNA targeting the region of the mRNA of said gene containing the following sequence: GGAGAUUCAUGGUGGCAUU (SEQ ID No.: 35) and/or an interfering RNA targeting the region of the mRNA of said gene containing the following sequence: GCCUUAGGGUUGCAUGAAU (SEQ ID No.: 36) can be used.

An interfering RNA directed against the region of the mRNA of the N gene containing a motif defined by the sequence SEQ ID No.: 19 will comprise a motif defined by the general sequence ARNGMNACCAWRAAYMKNC (SEQ ID No.: 37), and advantageously by the general sequence ARHGMBACCAURAAYCKSC (SEQ ID No.: 38).

An interfering RNA directed against a region of the mRNA of the N gene comprising a motif containing the general sequence SEQ ID No.: 21 will comprise a motif containing the general sequence AYUCRUGHARNSCNARDG (SEQ ID No.: 39). More particularly, if said interfering RNA is directed against the region of the mRNA of the N gene comprising the motif defined by the sequence SEQ ID No.: 22, it will comprise a motif defined by the general sequence AAYUCRUGHARNSCNARDG (SEQ ID No.: 40). If it is directed against the region of the mRNA of the N gene comprising the motif defined by the sequence SEQ ID No.: 23, it will comprise a motif defined by the general sequence AYUCRUGHARNSCNARDGC (SEQ ID No.: 41), and advantageously by the general sequence AYUCRUGHARNCCHARDGC (SEQ ID No.: 42).

As examples, to target the region of the mRNA of the gene N comprising the motif defined by the sequence SEQ ID No.: 19, it is possible to select.

in the case of the measles virus, an interfering RNA containing the following sequence: AGAGCGACCAUGAAUCGGC (SEQ ID No.: 43);

in the case of RPV, an interfering RNA containing the following sequence: AAUGCCACCAUAAAUCUGC (SEQ ID No.: 44);

in the case of PPRV, an interfering RNA containing the following sequence: AGAGAUACCAUGAACCGCC (SEQ ID No.: 45);

in the case of CDV, an interfering RNA containing the following sequence: AGCGCCACCAUGAAUCGCC (SEQ ID No.: 46);

in the case of PDV, an interfering RNA containing the following sequence: AAUGCCACCAUAAAUCGCC (SEQ ID No.: 47);

in the case of DMV, an interfering RNA containing the following sequence: AAUGCCACCAUGAAUCUCC (SEQ ID No.: 48).

Likewise, to target the region of the mRNA of the N gene comprising the motif defined by the sequence SEQ ID No.: 21, it is possible to select:

in the case of the measles virus, an interfering RNA containing the following sequence: AUUCAUGCAGUCCAAGAGC (SEQ ID No.: 49);

in the case of RPV, an interfering RNA containing the following sequence: AUCAUGCAGGCCCAGUGC (SEQ ID No.: 50);

in the case of PPRV, an interfering RNA containing the following sequence: ACUCGUGAAGGCCUAAUGC (SEQ ID No.: 51);

in the case of CDV, an interfering RNA containing the following sequence: ACUCAUGCAACCCAAGAGC (SEQ ID No.: 52);

in the case of PDV, an interfering RNA containing the following sequence: ACUCAUGUAGACCAAGUGC (SEQ ID No.: 53);

in the case of DMV, an interfering RNA containing the following sequence: AUUCAUGCAACCCUAAGGC (SEQ ID No.: 54).

For the implementation of the present invention, an interfering RNA targeting the region of the mRNA of the N gene comprising the sequence SEQ ID No.: 1, an interfering RNA targeting the region of the mRNA of the N gene comprising the sequence SEQ ID No.: 19, and an interfering RNA targeting the region of the mRNA of the N gene comprising the sequence SEQ ID No.: 21 can be used separately. Advantageously, a combination of interfering RNAs targeting two of these regions, or a combination of interfering RNAs targeting all three regions, can be used. Likewise, if necessary, one or more of these interfering RNAs can be used in combination with one or more other interfering RNAs targeting other regions of the morbillivirus genome.

Also a subject matter of the present invention are the interfering RNAs utilizable for the implementation of the process according to the invention, namely any interfering RNA directed against a region of the N gene of a morbillivirus containing a motif defined by one of the above general sequences SEQ ID No.: 1, SEQ ID No.: 19 and SEQ ID No.: 21.

More precisely, interfering RNAs according to the invention are:

interfering RNAs comprising a motif defined by the general sequence SEQ ID No.: 10, in particular those comprising a motif defined by the general sequence SEQ ID NO.: 11, or a motif defined by the general sequence SEQ ID No.: 12. As specific examples, the interfering RNAs comprising a motif defined by one of the sequences SEQ ID No.: 13 to SEQ ID No.: 18 will be cited;

interfering RNAs comprising a motif defined by the general sequence SEQ ID No.: 37, and advantageously by the general sequence SEQ ID NO.: 38. As specific examples, the interfering RNAs comprising a motif defined by one of the sequences SEQ ID No.: 43 to SEQ ID No.: 48 will be cited;

interfering RNAs comprising a motif defined by the general sequence SEQ ID No.: 39, in particular those comprising a motif defined by the general sequence SEQ ID No.: 40, or by the general sequence SEQ ID No.: 41, advantageously by the general sequence SEQ ID No.: 42. As specific examples, the interfering RNAs comprising a motif defined by one of the sequences SEQ ID No.: 49 to SEQ ID No.: 54 will be cited.

The different interfering RNAs defined above can take various forms.

It can be a single-strand, antisense RNA, capable of integrating into the RISC complex, and of pairing with the target sequence and inducing its cleavage (Tijsterman et al., Science, 295, 694, 2002; Martinez et al., Cell, 110, 563, 2002; Barik, Virus Res, 102, 27, 2004).

However, it will preferably be an RNA containing both the target sequence and the corresponding antisense sequence, in the form of siRNA, or if necessary sh ("short hairpin") RNAs (Yu et al., Proc Natl Acad Sci USA, 99, 6047, 2002; Paddison et al., Genes Dev, 16, 948, 2002; Siolas et al., Nat Biotechnol, 23, 227, 2005), which is transformed into siRNA in the cell.

The siRNAs generally have a length of 21 to 25 nucleotides; they contain a double-strand portion, generally of 19 to 21 nucleotides, made up of the target sequence and the corresponding antisense sequence; one strand or the other, or both, generally bear a single-strand extension of 2 or 3 nucleotides at the 3' end; most often, (but not obligatorily), this is a dinucleotide, of the sequence TT.

The siRNAs are made up of a single strand, of length 50 to 70 nucleotides, which can fold to form a hairpin structure, containing a double-strand portion of length 19 to 29 nucleotides, made up of the target sequence and the corresponding antisense sequence, and a loop of 5 to 10 nucleotides. They can likewise contain, at the 3' end, a single-strand extension of 2 or 3 nucleotides.

The interfering RNAs can also be used in the form of precursors of microRNAs (pre-miRNA). The microRNAs (miRNA) are RNAs of about 22 nucleotides, made up of a single strand and which attach themselves to the non-coding 3' end of the mRNA, which has the effect of suppressing the expression of that mRNA without degrading it (unlike the siRNAs or shRNAs). The miRNAs are important molecules for the "natural" regulation of the expression of genes in eukaryotic cells. The miRNAs are produced in the cytoplasm of the cells from nuclear precursors of about 70 nucleotides in the shape of a hairpin, called pre-miRNAs, cleaved into miRNAs by the DICER complex. The sequence of a pre-miRNA, identified under natural conditions in a eukaryotic cell, can be modified in order to introduce into it a siRNA sequence, which when liberated by DICER will then go to degrade another mRNA. This modified pre-miRNA then serves as a "vehicle" for the siRNA of interest, which has the result of increasing the efficacy of the interference. The possibility of using modified pre-miRNAs to inhibit viral replication has been demonstrated by Boden et al. (Nucleic Acids Res., 13, 1154, 2004) for HIV-1. In that case, the efficacy of the interference can be more than 80% of that conferred by the equivalent siRNA.

These interfering RNAs can be obtained by standard methods for preparation of nucleic acids (for review, see for example Amarzguoiou et al., FEBS Lett, 579, 5974, 2005).

They can thus be prepared for example by chemical synthesis, or else by genetic engineering. In this latter case, an expression vector containing a DNA sequence capable of transcription into an interfering RNA according to the invention, placed under the control of an appropriate promoter, will be used. Generally, said promoter is a viral promoter, for example the T3, T7, SP6 or pCMV promoter or a promoter recognized by polymerase III, for example the promoter of the small RNA U6, or that of the RNA H1 (Miyagishi & Taira, Nucleic Acids Res Suppl, 113, 2002); promoters recognized by polymerase II are however also utilizable.

The expression vectors defined above are also part of the subject matter of the present invention.

A very large number of methods for introducing interfering RNAs into cells or organisms in which it is desired to obtain the extinction of the expression of a target gene are known per se.

In the case where it is desired to obtain a temporary extinction of expression of the target gene, the interfering RNA can be administered directly, preferably combined with an appropriate vehicle, making it possible to facilitate its entry into the cell and/or to protect it from degradation. As examples of utilizable vehicles, liposomes or nanoparticles will in particular be cited.

To obtain a longer term extinction of the expression of the target gene, particularly in the case of mammalian cells, a vector making it possible to express the interfering RNA in the cell is used. A very large number of vectors utilizable for this purpose are known per se. In particular, vectors derived from retroviruses, from lentiviruses, or from adenoviruses (Barton & Medzhitov, Proc Natl Acad Sci USA, 99, 14943, 2002; Tiscornia et al., Proc Natl Acad Sci USA, 100, 1844, 2003; Xia et al., Nat Biotechnol, 20, 1006, 2002; Shen et al., FEBS Lett, 539, 111, 2003) will be cited.

Also a subject matter of the present invention is the use of an interfering RNA or of a expression vector according to the invention for the obtention of a medicament intended for the treatment or the prevention of a morbillivirus infection, and in particular for the treatment or the prevention of measles, rinderpest, small ruminant virus, Carré's disease, phocine distemper or a DMV infection.

Also a subject matter of the present invention is a pharmaceutical composition containing an interfering RNA or an expression vector according to the invention. Advantageously, said pharmaceutical composition is a vaccine.

The present invention will be better understood with the aid of the remainder of the description which will follow, which refers to examples illustrating the obtention of an interfering RNA according to the invention, and its utilization to block the replication of the morbilliviruses PPRV and RPV.

KEY TO DIAGRAMS

FIG. 1: Diagrammatic representation of the genome of the morbilliviruses.

Figure 2:
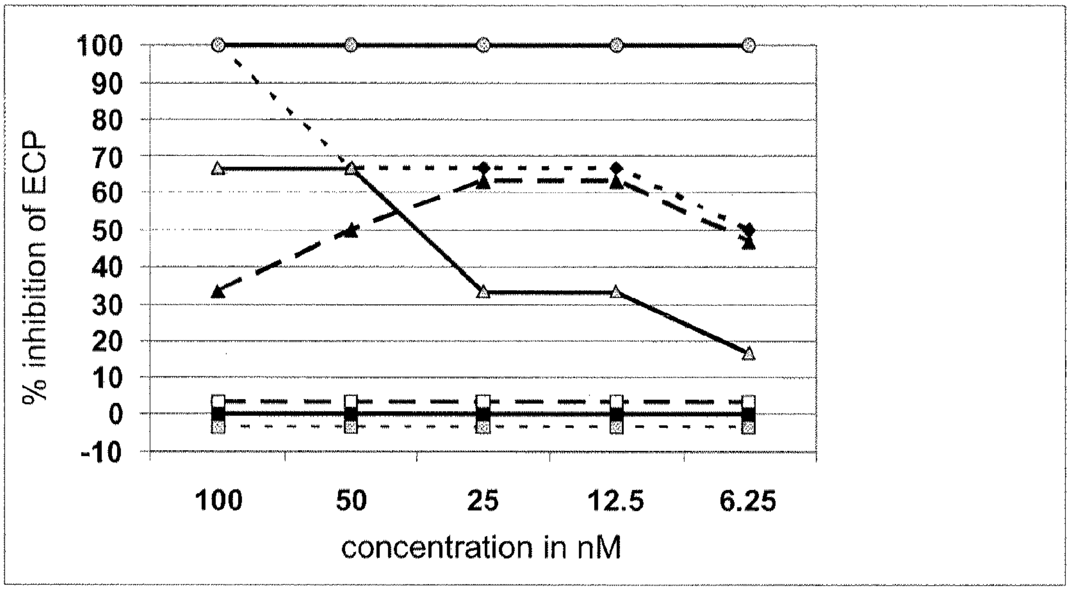

FIG. 2: Effect of siRNAs on the cytopathic effect (CPE) induced by the small ruminants virus on Vero cells. Y axis: scale of percentage inhibition of the CPE. X axis: concentration of siRNAs in nM.

--♦--: siRNA NPPR1; --□--: siRNA NPPR2; -—△—-: siRNA NPPR3; --▲--: siRNA NPPR10; -■-: siRNA GAPDH; -—※—-: non-infected cells; ---※---: infected, non-transfected cells.

Figure 3:
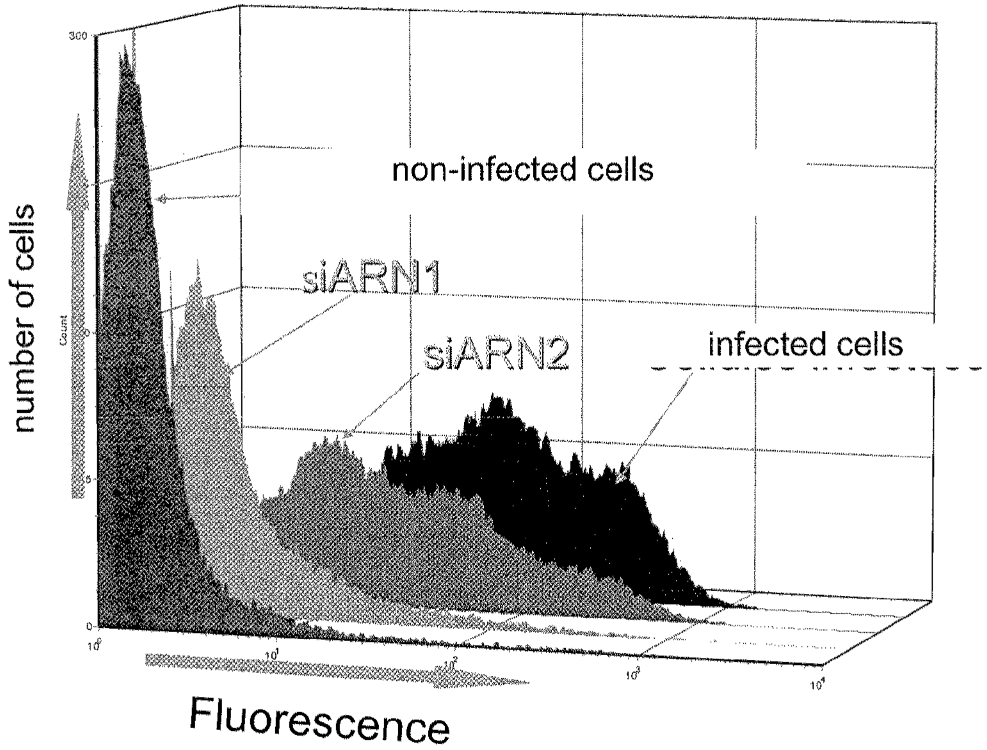
Figure 3:
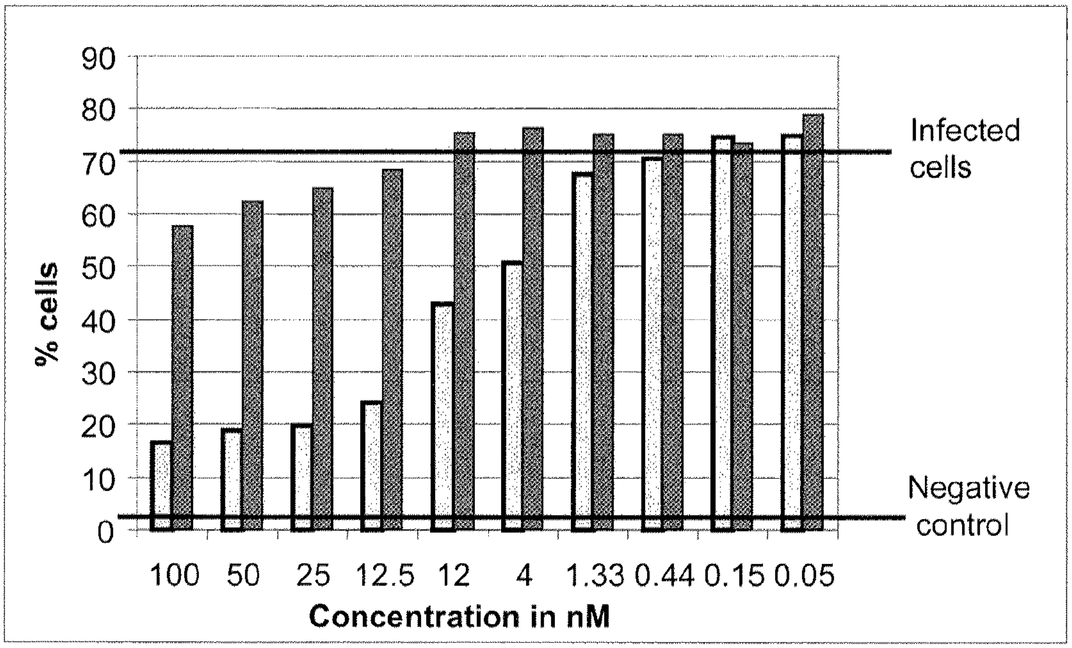

FIG. 3: Effect of siRNAs on the expression of PPRV virus N protein in Vero cells. (a) X axis: fluorescence linked with the expression of N protein; Y axis: number of fluorescent cells; siRNA1: siRNA NPPR1; siRNA2: siRNA NPPR2; non-infected cells: negative control; infected cells: positive control. (b) X axis: concentration (in nM) of siRNAs. Y axis: percentage of fluorescent cells;

□: siRNA NPPR1; ▩siRNA GAPDH.

Figure 4:
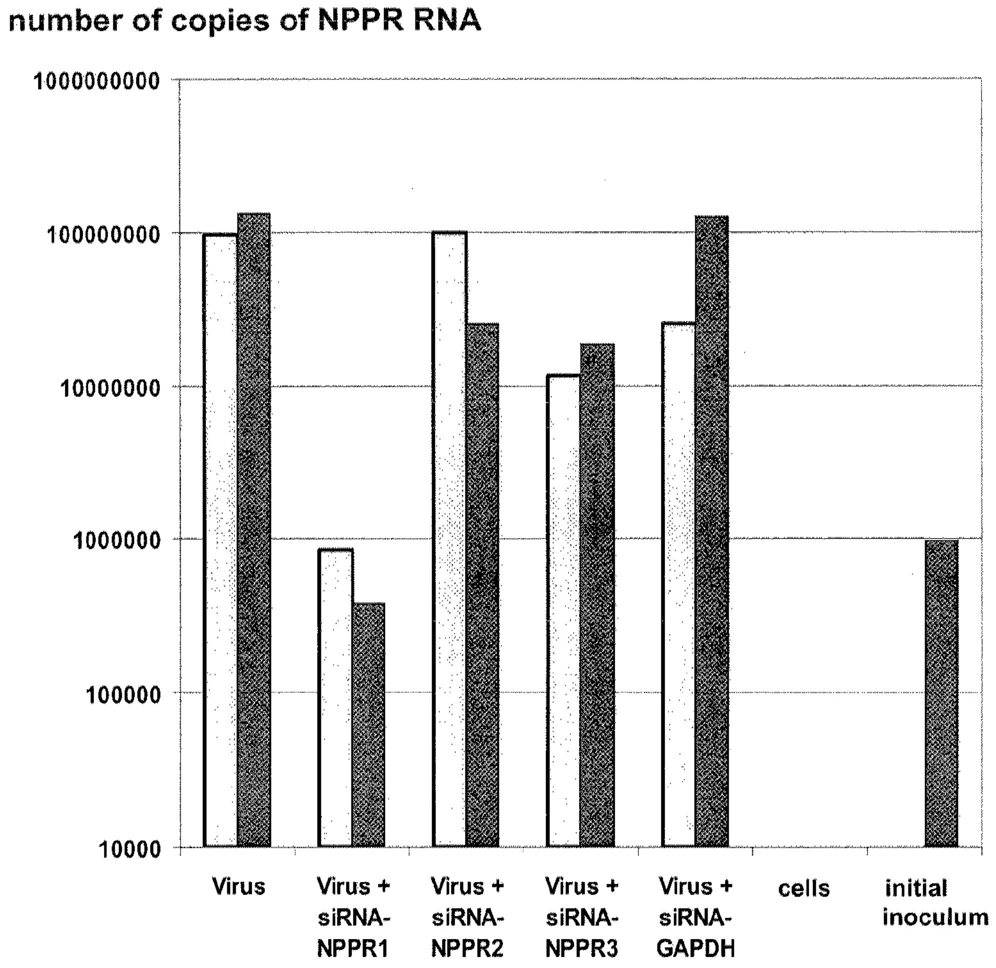

FIG. 4: Effect of the siRNAs NPPR1, 2 and 3 on the synthesis of viral RNAs measured by quantitative RT-PCR in real time (QRT-PCR). Representation of two independent experiments.

Figure 5:
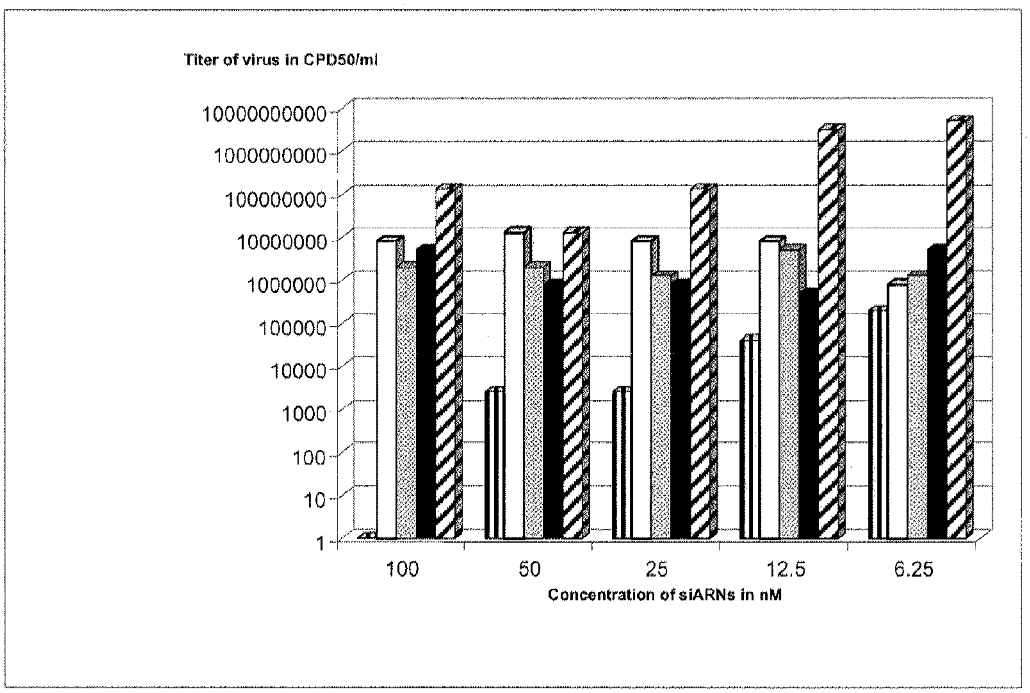

FIG. 5: Effect of the siRNAs NPPR1 (vertical hatching), NPPR2 (white), NPPR3 (gray), NPPR10 (black) and GAPDH (diagonal hatching) on the viral replication measured by the viral titer in infected cell sheets.

Figure 6:
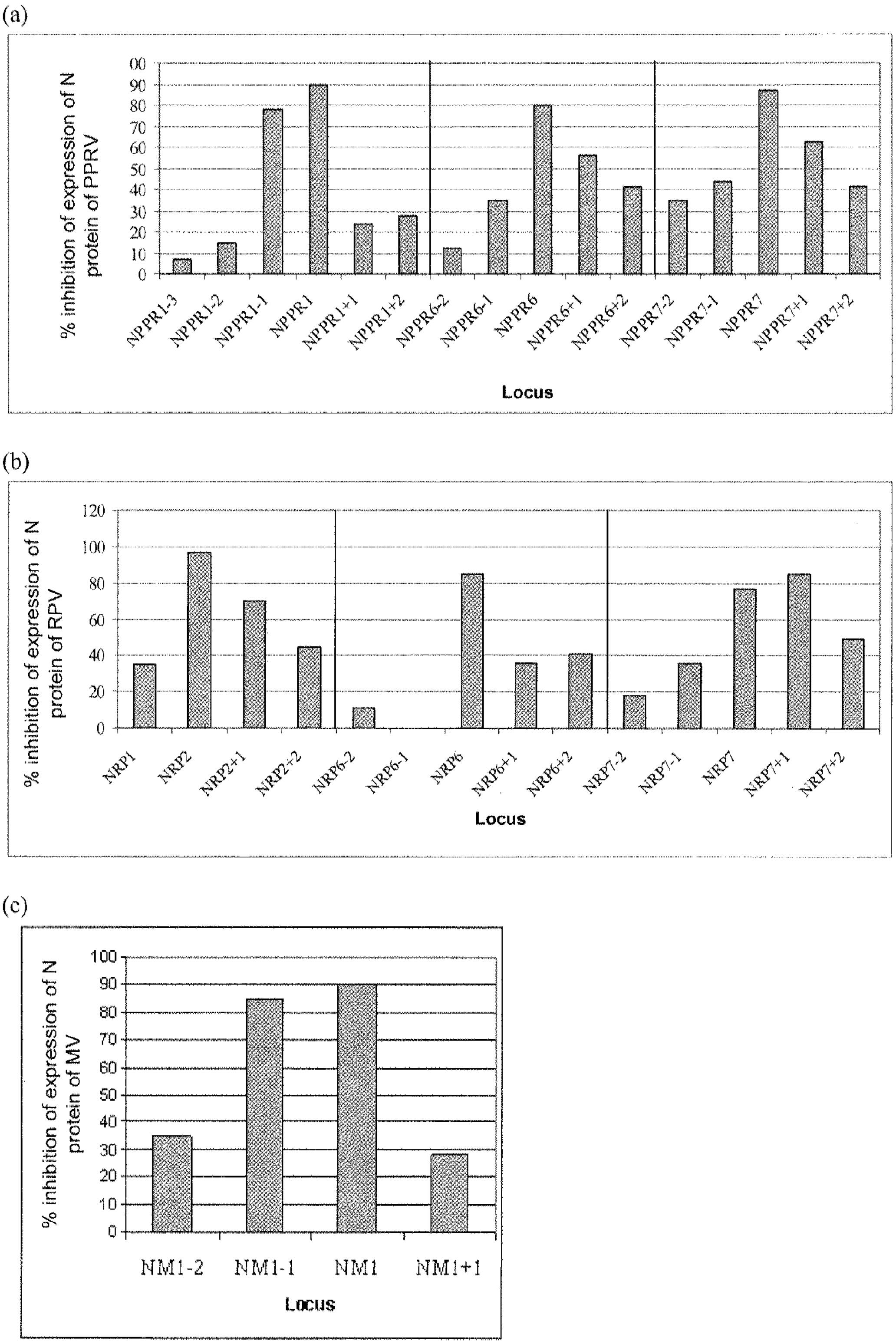

FIG. 6: Effect of siRNAs on the expression of the N proteins of PPRV, RPV and MV in Vero cells. (a) percentage inhibition of the N protein of PPRV as a function of the loci NPPR1−3 to NPPR1+2, NPPR6−2 to NPPR6+2 and NPPR7−2 to NPPR7+2; (b) percentage inhibition of the N protein of PRV as a function of the NRP1, NRP1+1 to NRP1+3, NRP6−2 to NRP6+2 and NRP7−2 to NRP7+2, (c) percentage inhibition of the N protein of MV as a function of the loci NMV1−2 to NMV1+1.

EXAMPLES

Material and Methods

1) Virus and Sequences of Interest

The PPRV virus utilized is the Nigeria 75/1 strain (Diallo et al. Rev Elev Med Vet Pays Trop 42, 311, 1989), attenuated by serial passages on cells (SK/1, BK/1 and Vero/55). It is a vaccine strain. The complete sequence of the genome of this strain is available on Genbank (access number X74443).

The RPV virus utilized is the RBOK strain (Plowright and Ferris, Res. Vet. Sci, 3, 172, 1962), a vaccine strain with virus attenuated by serial passages on cells (BK/98 and Vero/2). The complete sequence of the genome of this strain is available on Genbank (access number Z30697).

The MV virus utilized is the Schwarz strain. The complete sequence of the genome of this strain is available on Genbank (MVU03668).

The PPRV, RPV and MV viruses are proliferated on Vero cells (ATCC) maintained in monolayer in the presence of complete medium, namely: Eagle essential medium MEM with Earle salts (Eurobio, Courtaboeuf, France), 10% fetal bovine serum (Eurobio, Courtaboeuf, France) and 2 mM of L-glutamine (Gibco, Mife Technologies, UK).

2) Cell Culture, Transfection and Viral Infection

Adhering Vero cells are detached by means of a solution containing trypsin and EDTA (Sigma-Aldrich, Lyon, France) then resuspended in complete MEM (Minimum Eagle Medium) at the level of $10^5$ cells/ml and distributed into the wells of 24-well plates. The plates are incubated at 37° C. and 5% $CO_2$. Subsequently, all the cell incubations take place at 37° C. in the presence of 5% $CO_2$. When the cell sheet reaches 70-80% confluence, the medium is removed, then the cells are incubated for 30 minutes in MEM medium containing no fetal bovine serum.

For the transfection, the medium is removed and replaced by Lipofectamine™ 2000 (Invitrogen) at the level of 500 ng in 200 μl of transfection medium Opti-Mem I® (Invitrogen) containing the siRNA at different concentrations (from 6.5 to 100 nM final in the transfection mixture). The next incubation takes place for three hours.

For the viral infection, the transfection medium is removed and replaced by MEM and 5% fetal bovine serum. The cells are incubated for 24 hours then infected with the MV, PPRV or RPV virus at an infection multiplicity of 0.1 cytopathic dose 50% per cell, in a medium with no fetal bovine serum, the cytopathic dose 50% being the quantity of virus inducing a CPE on 50% of the cell sheets infected. After one hour of contact, the cell sheet is rinsed twice with MEM medium, then MEM medium with 5% fetal bovine serum is added onto the cells. The cells are observed daily and the course of the cytopathic effect (CPE) due to the virus is evaluated on the basis of a percentage grid (scale ranging from 0%, no CPE to 100%, maximal CPE). The effect of the siRNA is expressed as percentage inhibition of CPE.

Four to five days after infection, the cell culture supernatant on the one hand, and the cells on the other hand are collected for analysis by viral titration and by flow cytometry for expression of viral antigens. Controls consisting of non-transfected and non-infected cells and infected and non-transfected cells are included in each series of tests of the siRNAs.

4) Viral Titration

The cell culture supernatants or the cells themselves are stored at −70° C. until utilization for titration. The viral titration is effected on cell culture (Vero) on the basis of a ten-fold dilution series of the viral suspension to be titrated. The titer is determined by the method of Reed and Muench (Am J Trop Med Hyg, 127, 493, 1938) and expressed as cytopathic dose 50 ($CPD_{50}$) par ml.

5) Measurement of the Expression of Viral Antigens

The expression of the viral nucleocapsid (N), matrix (M) and fusion (F) proteins was measured by flow cytometry using specific monoclonal antibodies: antibody 38-4 specific for the N protein of PPRV; antibody IVB2-4 specific for the N protein of RPV; antibodies MAB8906 (Chemicon International) specific for the N protein of MV, antibody 19-6 specific for the M protein of PPRV and the M protein of RPV (Libeau et al., Revue d'Elevage et de Médecine Vétérinaire des Pays Tropicaux, 50, 181-190, 1997), antibodies MAB 128-1 specific for the F protein of RPV (Libeau et al., Revue d'Elevage et de Médecine Vétérinaire des Pays Tropicaux, 50, 181-190, 1997) and antibody 11/295/33 specific for the molecule porcine lymphocyte CD8 (Saalmuller et al., Vet Immunol Immunopathol, 43, 249, 1994) utilized as an isotypic control of labeling specificity.

The adherent cells are detached from the plastic by incubation with a solution containing trypsin and EDTA for 5 minutes at 37° C. The cells are washed in PBS phosphate buffer, 0.1% sodium azide, 5% horse serum and 0.0062% saponin (weight/volume). They are counted and distributed at a level of $10^6$ cells per well of a 96-well plate. All labeling is performed on the plate. After sedimentation of the cells by centrifugation and removal of the supernatant, 100 μl of an appropriate dilution of the monoclonal anti-N, anti-M or isotypic antibody are added and the cells resuspended by mechanical stirring. The cells are incubated for 30 minutes at +4° C. They are next washed twice in the same phosphate buffer, then incubated for 30 minutes at +4° C., in 50 μl of an appropriate dilution of an anti-mouse-antibody antibody, conjugated with fluorescein (Biorad, France). The cells are washed twice then fixed for 15 minutes at ambient temperature with 100 μl of a solution of paraformaldehyde. The cells are resuspended in 400 μl of FACS FLOW PBS (Becton Dickinson, USA). The analysis of the cells is performed on the FACsort (Becton Dickinson, USA). The cell debris is removed from the FACS analysis by a fenestration placed on FSCxSSC (FSC: Forward SCatter; SSC: Side SCatter), then the fluorescence is measured on 20 000 cells.

6) Quantitative Measurement of the Synthesis of Viral RNAs

The cells and the culture supernatant are harvested 96 hours after infection and frozen at −70° C. The total RNA is extracted from 100 μl of this cell suspension mixed with the lysis solution of the RNeasy kit, according to the manufacturer's instructions (Qiagen, Courtaboeuf, France). The rest of the protocol corresponds to the manufacturer's instruction manual. The extracted RNA is stored at −70° C. The RNA is quantified by one step QRT-PCR (Brilliant SYBR Green QRT-PCR Master Mix, 1 step, Stratagene). The primers utilized are NP3bis=5'-GTCTCGGAAATCGCCTCACAG-3' (sense) (SEQ ID No.: 55) and NP4bis=5'-CCTCCTCCTG-GTCCTCCAGAA-3' (antisense) (SEQ ID No.: 56). These primers were derived from previously described primers (Couacy-Hymann et al., J Virol Methods, 100, 17, 2002) by addition of a G at 5' of NP3bis and deletion of four bases at 3' and deletion of three bases at 3' of NP4bis. These primers amplify a fragment of 351 bases. A principal reaction solution made up of 12.5 μl of SYBR Green Master mix (2×), 2.5 μl of 1 μM of each primer, 0.0625 μl of Stratascript Reverse Transcriptase RT and 2.4375 μl of water is deposited into a microtube, then 5 μl of the RNA extract are added. The QRT-PCR is carried out on a Mx3000P apparatus (Stratagene, Amsterdam, NL) according to the following protocol:

- reverse transcription at 50° C. for 30 minutes
- denaturation at 95° C. for 10 minutes
- amplification with 35 cycles [95° C., 30 seconds; 55° C., 1 minute; 72° C., 30 seconds]
- dissociation with one cycle [95° C., 1 minute; 55° C., 30 seconds; 95° C., 30 seconds]

The standard reference for the quantification is made up of the gene for the N protein of PPRV inserted into a pBluescript KS+ plasmid (Couacy-Hymann et al., 2002, previously cited). For the quantification, the plasmid is linearized, purified by alcohol precipitation and serially diluted from 10 to 10. The quantity of RNA detected in the samples subjected to analysis is expressed as the number of copies of N gene incorporated in the dilution series of the standard reference.

Example 1

Selection and Synthesis of siRNAs

The conserved zones of the N gene were located by multiple alignment of the corresponding sequences derived from different morbilliviruses with the aid of sequence analysis software (Vector NTI package, Informax Inc). This multiple alignment of sequences was performed on the sequences of the N genes of the morbilliviruses whose GenBank access numbers are as follows:

PPRV: X74443 and AY560591, for RPV: AF378110, Z30697, E06018, X98291, for PDV: X75717, for DMV: AJ608288, for CDV: AF014953, AF164967, AF166268, AF166269, AF166270, AF166271, AF166272, AF166273, AF378705, AY238607, AY241572, AY241573, AY241574, AY241575, AY241576, AY241577, AY241578, AY241579, AY241580, AY241581, AY241582, AY278994, AY278995, AY386315, AY386316, AY390348, AY443350, AY445077, AY466011, AY542312, AY684629, AY738624, AY738625, AY738653, AJ009656, DQ003302, DQ005126, DQ005127, DQ005128, DQ005129, DQ005130, DQ005131, DQ005132, DQ005133, DQ005134, DQ435615, DQ522030, DQ887066, DQ887333, NC_001921 and X02000, and for MV: AB012948, AB012949, AB016162, AB032167, AB046218, AB052821, AB254456, AF045205, AF045206, AF045207, AF045208, AF045209, AF045210, AF045211, AF045212, AF045213, AF045214, AF045215, AF045216, AF045217, AF045218, AF079555, AF171232, AF243852, AF266286, AF266287, AF266288, AF266289, AF266290, AF266291, AF280800, AF280801, AF280802, AF280803, AF280804, AF417265, AF417266, AF417267, AF417268, AF417269, AF417270, AF417271, AF419319, AF440685, AF440686, AF440687, AF504045, AF504046, AF504047, AF504048, AF504049, AY027637, AY027638, AY027639, AY027640, AY027641, AY027642, AY027643, AY027644, AY184217, AY486083, AY486084, AY556539, AY556540, AY556541, AY556542, AY730614, DQ011612, DQ011613, DQ190373, DQ211902, DQ227318, DQ227319, DQ227320, DQ227321, DQ345721, DQ345723, X16566, X16567, X16568, X16569, D63927, M89921, M89922, L46728, L46730, L46733, L46735, L46740, L46742, L36042, L36046, L46744, L46746, L46748, L46750, L46753, L46756, L46758, L46760, L46764, L46767, Z66517, AJ232191, AJ232192, AJ232193, AJ232194, AJ232195, AJ232196, AJ232197, AJ232198, AJ232199, AJ232200, AJ232201, AJ232202, AJ232203, AJ232204, AJ232205, AJ232206, AJ232207, AJ232208, AJ232209, AJ232210, AJ232211, AJ232212, AJ232213, AJ232214, AJ232215, AJ232216, AJ232217, AJ232218, AJ232219, AJ232220, AJ232221, AJ232770, AJ232771, AJ232772, AJ232773, AJ232774, AJ232775, AJ232776, AJ232777, AJ232778, AJ232779, AJ232780, AJ232781, AJ232782, AJ244027, AJ244028, AJ244029, AJ244030, AJ244031, AJ244032, AJ244033, AJ244034, AJ244035, AJ244036, AJ244037, AJ244038, AJ244039, AJ244040, AJ244041, AJ250068, AJ250069, AJ250070, AJ250071, AJ250072, AJ250073, U01974, U01976, U01977, U01978, U01987, U01988, U01989, U01990, U01991, U01992, U01993, U01994, U01995, U01996, U01998, U01999, U03650, U03653, U03656, U03658, U03661, K01711, U03664, U03668, U29317, U97350, AF266287, X01999, X13480, D10550 and S58435.

In the regions exhibiting the highest degree of homology, 7 target sequences were defined for the virus PPRV.

The siRNAs derived from the N gene of the virus PPRV, and containing sequences identical to the target sequences defined in this gene, are named NPPR1, and NPPR5 to 10; one siRNA named NPPR2, at the best only displaying 58% identity with the sequence of the N gene of the virus PPRV (in positions 256-274, 751-769, and 850-869 of the cDNA sequence), and one siRNA named NPPR3, derived from the same target sequence as the siRNA NPPR10, but displaying a difference of one base from said target sequence (C in the target sequence replaced by G at the 5' end of the sense strand of the siRNA NPPR3) were also synthesized.

For the virus RPV, 4 target sequences were defined at the level of the loci corresponding to the target sequences of siRNA-NPPR1, siRNA-NPPR6 and siRNA-NPPR7. The corresponding siRNAs are named NRP1, NRP1+1, NRP6 and NRP7. NRP1+1 corresponds to NRP1 shifted one base towards the 3' end.

For the virus MV, 1 target sequence was defined at the level of the locus corresponding to the target sequence of siRNA-NPPR1. The corresponding siRNA is named NM1.

All the siRNAs mentioned above were chemically synthesized by the company Ambion (Europe) (Cambridgeshire, UK).

To test the specificity of the interference, a siRNA targeting the sequence of glyceraldehyde-3-phosphate dehydrogenase (GAPDH) was utilized: the sequence and the siRNA are available from Ambion (Europe) (Silencer™ GAPDH siRNA (Human) Control 4605).

All the siRNA sequences identified were subjected to a homology search in Genbank by means of the Blast software. The maximum identity observed between the siRNA-GAPDH and the sequence coding for the N protein of the virus PPRV is 72%.

The sequences of the sense and antisense strands of the different siRNAs mentioned above, and their positions relative to the sequence of cDNA of the N gene and relative to the sequence of the reading frame of said gene, are indicated in Table I below.

TABLE I

| Name of siRNA | Sequence (SEQ ID #) | | Position in the cDNA/in the reading frame |
|---|---|---|---|
| siRNA-NPPR1 | sense: 5'-GGAUCAACUGGUUUGAGAAtt-3' | (57) | 480-498/428-446 |
| | antisense: 5'-UUCUCAAACCAGUUGAUCCtt-3' | (58) | |
| siRNA-NPPR2 | sense: 5'-GCUCACCUUCAUUCUUUUCtt-3' | (59) | —/— |
| | antisense: 5'-GAAAAGAAUGAAGGUGAGCtc-3' | (60) | |
| siRNA-NPPR3 | sense: 5'-GGCCAGUUUCAUUCUUACUtt-3' | (61) | 850-868/798-816 |
| | antisense: 5'-AGUAAGAAUGAAACUGGCCtc-3' | (62) | |
| siRNA-NPPR5 | sense: 5'-GAGAACUCAAUUCAGAACAtt-3' | (63) | 1001-1019/949-968 |
| | antisense: 5'-UGUUCUGAAUUGAGUUCUCtt-3' | (64) | |
| siRNA-NPPR6 | sense: 5'-GGCGGUUCAUGGUAUCUCUtt-3' | (65) | 741-759/689-707 |
| | antisense: 5'-AGAGAUACCAUGAACCGCCtt-3' | (66) | |
| siRNA-NPPR7 | sense: 5'-GCAUUAGGCCUUCACGAGUtt-3' | (67) | 899-917/847-865 |
| | antisense: 5'-ACUCGUGAAGGCCUAAUGCtt-3' | (68) | |
| siRNA-NPPR8 | sense: 5'-GUAUCAACAGCUAGGAGAGtt-3' | (69) | 958-976/906-924 |
| | antisense: 5'-CUCUCCUAGCUGUUGAUACtt-3' | (70) | |
| siRNA-NPPR9 | sense 5'-GAACUUUGGCAGGUCAUAUtt-3' | (71) | 1102-1120/1050-1068 |
| | antisense: 5'-AUAUGACCUGCCAAAGUUCtt-3' | (72) | |
| siRNA-NPPR10 | sense: 5'-CGCCAGUUUCAUUCUUACUtt-3' | (73) | 850-868/798-816 |
| | antisense 3'-AGUAAGAAUGAAACUGGCGtt-3' | (74) | |
| siRNA-NRP1 | sense: 5'-GCAGUCUUACUGGUUUGAGtt-3' | (75) | 478-496/426-444 |
| | antisense: 5'-CUCAAACCAGUAAGACUGCtt-3' | (76) | |
| siRNA-NRP1 + 1 | sense: 5'-CAGUCUUACUGGUUUGAGAtt-3' | (77) | 479-497/427-445 |
| | antisense: 5'-UCUCAAACCAGUAAGACUGtc-3' | (78) | |
| siRNA-NRP6 | sense: 5'-GCAGAUUUAUGGUGGCAUUtt-3' | (79) | 741-759/689-707 |
| | antisense: 5'-AAUGCCACCAUAAAUCUGCtt-3' | (80) | |
| siRNA-NRP7 | sense: 5'-GCACUGGGCCUGCAUGAAUtt-3' | (81) | 899-917/847-865 |
| | antisense: 5'-AUUCAUGCAGGCCCAGUGCtt-3' | (82) | |

TABLE I-continued

| Name of siRNA | Sequence (SEQ ID #) | | Position in the cDNA/in the reading frame |
|---|---|---|---|
| siRNA-NM1 | sense: 5'-GGUUCGGAUGGUUCGGGAAtt-3' | (83) | 480-498/428-446 |
| | antisense: 5'-UUCCCGAACCAUCCGAACCtt-3' | (84) | |
| siRNA-GAPDH | sense: 5'-AAGGUCAUCCAUGACAACUtt-3' | (85) | —/— |
| | antisense: 5'-AGUUGUCAUGGAUGACCUUtt-3' | (86) | |

Example 2

Effect of the siRNAs NPPR1, 2, and 3 and of siRNA-GAPDH on the Cytopathic Effect of the Small Ruminants Virus Vero cells were transfected with different doses of the siRNAs NPPR1, 2, and 3 or of siRNA-GAPDH, then infected with PPRV, according to the protocol described in the section "Material and Methods"; 4 days after infection, the cytopathic effect was assessed independently by two different people.

FIG. 2 illustrates the results observed:

Among the siRNAs tested, the siRNA NPPR1 is the one that most inhibits the CPE, whatever the dose utilized. At the dose of 100 nM, complete inhibition of the CPE is observed. The siRNA NPPR3, the sequence of which varies by one nucleotide relative to the target sequence defined on the virus (cf. Example 1) inhibits the CPE less markedly than NPPR1. The siRNA NPPR10, which is directed against the same target sequence as the siRNA NPPR3, but which, unlike the latter, is perfectly complementary to said target sequence, likewise inhibits the CPE less markedly than NPPR1 (results not shown).

As expected, the siRNA-NPPR2 and the siRNA-GAPDH do not produce any neutralization of the CPE.

Example 3

Effect of the siRNA on the Expression of the N Protein and M Protein of PPRV and of RPV Vero cells were transfected with different doses of the siRNA NPPR1, the siRNA NPPR2 or the siRNA GAPDH, then infected with PPRV, as described in the section "Material and Methods"; 4 to 5 days after infection, the production of the N protein in the cells is measured by flow cytometry, as described in the section "Material and Methods".

FIG. 3 (*a*) illustrates the results observed in cells transfected with 100 nM of the siRNA NPPR1 or the siRNA NPPR2, and in non-infected and non-transfected cells, and in non-transfected and infected cells, used as controls. A very strong inhibition of the expression of the N protein is observed in the infected cells transfected with the siRNA NPPR1, whereas in those transfected with the siRNA NPPR2, the expression profile of the N protein is very similar to that observed with the infected, non-transfected cells, although a certain diminution of the expression is observed.

FIG. 3 (*b*) illustrates the results observed in cells transfected with different doses of the siRNA NPPR1 or the siRNA GAPDH. Beyond 12.5 nM of siRNA NPPR1, a very significant diminution in the percentage of cells expressing the N protein is observed.

In a second series of experiments, the expression of the N protein and of the M protein was measured:

- in Vero cells transfected with the optimal dose for each of the siRNAs tested, namely 100 nM for the siRNAs NPPR1, 2, 3, or 5 to 9, or 25 nM for the siRNA NPPR10, then infected with PPRV or with RPV;
- in Vero cells transfected with 100 nM of one of the siRNAs NRP1 or NRP1+1, then infected with PPRV or with RPV.

The measurement of the expression of the M protein makes it possible to confirm that the inhibition of the expression of the N protein results in inhibition of the other viral proteins, which exerts an effect on the replication of the viral genome.

The results of one experiment are summarized in Table II below.

TABLE II

| Nature of siRNA (optimal concentration) | Inhibition of the expression of the PPRV nucleoprotein (in %) | Inhibition of the expression of the PPRV matrix protein (in %) | Inhibition of the expression of the RPV nucleoprotein (in %) | Inhibition of the expression of the RPV matrix protein (in %) | SEQ ID NO: |
|---|---|---|---|---|---|
| siRNA-NPPR1 (100 nM) | 90 | 89 | 0 | 0 | 57 |
| siRNA-NPPR2 (100 nM) | 25 | 11 | nt | nt | 59 |
| siRNA-NPPR3 (100 nM) | 40 | 30 | nt | nt | 61 |
| siRNA-NPPR5 (100 nM) | 16 | nt | nt | nt | 63 |
| siRNA-NPPR6 (100 nM) | 68 | nt | nt | nt | 65 |
| siRNA-NPPR7 (100 nM) | 63 | nt | nt | nt | 67 |
| siRNA-NPPR8 (100 nM) | 34 | nt | nt | nt | 69 |
| siRNA-NPPR9 (100 nM) | 35 | nt | nt | nt | 71 |
| siRNA-NPPR10 (25 nM) | 60 | 55 | nt | nt | 72 |
| siRNA-NRP1 (100 nM) | 0 | nt | 35 | 31 | 75 |
| siRNA-NRP1 + 1 (100 nM) | 0 | nt | 97 | 92.5 | 77 |
| siRNA-GAPDH (100 nM) | 0 | 5 | 13 | 3 | 85 |

nt: not tested

In this experiment, four of the siRNA tested (siRNAs NPPR1, 6, 7 and 10) have a significant effect on PPRV. Among these, only the siRNA NPPR1 makes it possible to attain a percentage inhibition of the expression of the N protein of 90% (the other siRNAs do not make it possible to attain 70% inhibition of expression) and a percentage inhibition of the expression of the M protein of 89%.

As regards RPV, only the siRNA NRP1+1 has a significant effect. The siRNA NRP1, which does not contain the entirety of the target sequence, has a much diminished effect.

These results show that the locus recognized by the siRNAs NPPR1, and NRP1+1 constitutes a particularly interesting target for the extinction of the gene for the N protein of the morbilliviruses. This target is very circumscribed, since one missing base considerably decreases the effects obtained.

Example 4

Inhibitory Effect of the siRNA NPPR1 on the Synthesis of Viral RNAs

The effect of the siRNA NPPR1 on viral replication was evaluated by quantifying the synthesis of the viral RNA, as described in the section "Material and Methods", in Vero cells infected with PPRV, non-transfected, or transfected with 100 nM of one of the siRNAs NPPR1, NPPR3, NPPR2 or GAPDH, and in non-infected Vero cells.

The results are illustrated by FIG. 4.

In the infected, non-transfected cells, the viral replication results in a quantity of viral RNA 100 times greater than that contributed by the initial inoculum. Transfection with the siRNAs NPPR2 and GAPDH had no significant effect on the viral replication. In the cells transfected with NPPR3, the quantity of viral RNA remains more than 10 times greater than that contributed by the initial inoculum. On the other hand, in the cells transfected with NPPR1, the quantity of viral RNA corresponds to that contributed by the initial inoculum, which confirms that this siRNA inhibits the viral replication.

Example 5

Inhibitory Effect of the siRNA NPPR1 on Viral Replication Measured by the Viral Titer The effect of the siRNA NPPR1 on viral replication was evaluated by measuring the viral titer, as described in "Materials and Methods", 4 days after the infection with PPRV of Vero cells transfected with 6.25, 12.5, 25, 50 or 100 nM of one of the siRNAs NPPR1, NPPR2, NPPR3, NPPR10 or GAPDH.

The results are illustrated by FIG. 5.

For the cells transfected with one of the siRNAs NPPR2, NPPR3 and NPPR10, a slight diminution in the viral titer relative to the control (cells transfected with the siRNA GAPDH), which does not vary significantly as a function of the concentration tested, is observed.

For the cells transfected with NPPR1, the viral titer diminishes very significantly beyond 12.5 nM of siRNA. At 100 nM of siRNA, total inhibition of viral replication is observed.

Example 6

Demarcation of the Effective Loci in the N Genes of PPRV, RPV and MV

To define the exact location of the most effective loci, siRNA were defined by displacement by one (+1), two (+2), or three (+3) 3' bases or one (−1), two (−2), or three (−3) 5' bases relative to the loci defined in Example 1 (cf. Table I).

For the virus PPRV the siRNA tested are:

NPPR1, NPPR1−3, NPPR1−2, NPPR1−1, NPPR1+1 and NPPR1+2,

NPPR6, NPPR6−2, NPPR6−1, NPPR6+1 and NPPR6+2,

NPPR7, NPPR7−2, NPPR7−1, NPPR7+1 and NPPR7+2.

For the virus RPV the siRNA tested are:

NRP1, NRP1+1, NRP1+2, NRP1+3

NRP6, NRP6−2, NRP6−1, NRP6+1 and NRP6+2,

NRP7, NRP7−2, NRP7−1, NRP7+1 and NRP7+2.

For the virus MV the siRNA tested are NM1, NM1−2, NM1−1 and NM1+1.

The sequences of the sense and antisense strands of the different siRNAs mentioned above, and their position relative to the sequence of the Y gene and relative to the sequence of the reading frame of said gene, are indicated in Table III below.

TABLE III

| Name of siRNA | SEQUENCE (SEQ ID #) | | Position in the cDNA/in the reading frame |
|---|---|---|---|
| siRNA-NPPR1 − 3 | sense: 5'-AAAGGAUCAACUGGUUUGAtt-3' | (87) | 477-495/425-443 |
| | antisense: 5'-UCAAACCAGUUGAUCCUUUtc-3' | (88) | |
| siRNA-NPPR1 − 2 | sense: 5'-AAGGAUCAACUGGUUUGAGtt-3' | (89) | 478-496/426-444 |
| | antisense: 5'-CUCAAACCAGUUGAUCCUUtt-3' | (90) | |
| siRNA-NPPR1 − 1 | sense: 5'-AGGAUCAACUGGUUUGAGAtt-3' | (91) | 479-497/427-445 |
| | antisense: 5'-UCUCAAACCAGUUGAUCCUtt-3' | (92) | |
| siRNA-NPPR1 + 1 | sense: 5'-GAUCAACUGGUUUGAGAACtt-3' | (93) | 481-499/429-447 |
| | antisense: 5'-GUUCUCAAACCAGUUGAUCtt-3' | (94) | |
| siRNA-NPPR1 + 2 | sense: 5'-AUCAACUGGUUUGAGAACAtt-3' | (95) | 482-500/430-448 |
| | antisense: 5'-UGUUCUCAAACCAGUUGAUtc-3' | (96) | |

TABLE III-continued

| Name of siRNA | SEQUENCE (SEQ ID #) | | Position in the cDNA/in the reading frame |
|---|---|---|---|
| siRNA-NPPR6 − 2 | sense: 5'-UCGGCGGUUCAUGGUAUCUtt-3' | (97) | 739-757/687-705 |
| | antisense: 5'-AGAUACCAUGAACCGCCGAtt-3' | (98) | |
| siRNA-NPPR6 − 1 | sense: 5'-CGGCGGUUCAUGGUAUCUCtt-3' | (99) | 740-758/688-706 |
| | antisense: 5'-GAGAUACCAUGAACCCCCGtt-3' | (100) | |
| siRNA-NPPR6 + 1 | sense: 5'-GCGGUUCAUGGUAUCUCUCtt-3' | (101) | 742-760/690-708 |
| | antisense: 5'-GAGAGAUACCAUGAACCGCtt-3' | (102) | |
| siAR-NPPR6 + 2 | sense: 5'-CGGUUCAUGGUAUCUCUCAtt-3' | (103) | 743-761/691-709 |
| | antisense: 5'-UGAGAGAUACCAUGAACCGtt-3' | (104) | |
| siRNA-NPPR7 − 2 | sense: 5'-CUGCAUUAGGCCUUCACGAtt-3' | (105) | 897-915/845-863 |
| | antisense: 5'-UCGUGAAGGCCUAAUGCAGtt-3' | (106) | |
| siRNA-NPPR7 − 1 | sense: 5'-UGCAUUAGGCCUUCACGAGtt-3' | (107) | 898-916/846-864 |
| | antisense: 5'-CUCGUGAAGGCCUAAUGCAtt-3' | (108) | |
| siRNA-NPPR7 + 1 | sense: 5'-CAUUAGGCCUUCACGAGUUtt-3' | (109) | 900-918/848-866 |
| | antisense: 5'-AACUCGUGAAGGCCUAAUGtt-3' | (110) | |
| siRNA-NPPR7 + 2 | sense: 5'-AUUAGGCCUUCACGAGUUGtt-3' | (111) | 901-919/849-867 |
| | antisense: 5'-CAACUCGUGAAGGCCUAAUtt-3' | (112) | |
| siRNA-NRP6 − 2 | sense: 5'-ACGCAGAUUUAUGGUGGCAtt-3' | (113) | 739-757/687-705 |
| | antisense: 5'-UGCCACCAUAAAUCUGCGUtt-3' | (114) | |
| siRNA-NRP6 − 1 | sense: 5'-CGCAGAUUUAUGGUGGCAUtt-3' | (115) | 740-758/688-706 |
| | antisense: 5'-AUGCCACCAUAAAUCUGCGtt-3' | (116) | |
| siRNA-NRP6 + 1 | sense: 5'-CAGAUUUAUGGUGGCAUUGtt-3' | (117) | 742-760/690-708 |
| | antisense: 5'-CAAUGCCACCAUAAAUCUGtt-3' | (118) | |
| siRNA-NRP6 + 2 | sense: 5'-AGAUUUAUGGUGGCAUUGAtt-3' | (119) | 743-761/691-709 |
| | antisense: 5'-UCAAUGCCACCAUAAAUCUtt-3' | (120) | |
| siRNA-NRP7 − 2 | sense: 5'-CAGCACUGGGCCUGCAUGAtt-3' | (121) | 897-915/845-863 |
| | antisense: 5'-UCAUGCAGGCCCAGUGCUCtt-3' | (122) | |
| siRNA-NRP7 − 1 | sense: 5'-AGCACUGGGCCUGCAUGAAtt-3' | (123) | 898-916/846-864 |
| | antisense: 5'-UUCAUGCAGGCCCAGUGCUtt-3' | (124) | |
| siRNA-NRP7 + 1 | sense: 5'-CACUGGGCCUGCAUGAAUUtt-3' | (125) | 900-918/848-866 |
| | antisense: 5'-AAUUCAUGCAGGCCCAGUGtt-3' | (126) | |
| siRNA-NRP7 + 2 | sense: 5'-ACUGGGCCUGCAUGAAUUCtt-3' | (127) | 901-919/849-867 |
| | antisense: 5'-GAAUUCAUGCAGGCCCAGUtt-3' | (128) | |
| siRNA-NRP1 + 2 | sense: 5'-AGUCUUACUGGUUUGAGAAtt-3' | (129) | 480-498/428-446 |
| | antisense: 5'-UUCUCAAACCAGUAAGACUtc-3' | (130) | |
| siRNA-NRP1 + 3 | sense: 5'-GUCUUACUGGUUUGAGAAUtt-3' | (131) | 481-499/429-447 |
| | antisense: 5'-CCCGAACCAUCCGAACCUGtt-3' | (132) | |
| siRNA-NM1 − 2 | sense: 5'-CAGGUUCGGAUGGUUCGGGtt-3' | (133) | 478-496/427-444 |
| | antisense: 5'-UUCUCAAACCAGUAAGACUtc-3' | (134) | |

TABLE III-continued

| Name of siRNA | SEQUENCE (SEQ ID #) | | Position in the cDNA/in the reading frame |
|---|---|---|---|
| siRNA-NM1 − 1 | sense: 5'-AGGUUCGGAUGGUUCGGGAtt-3' | (135) | 479-497/427-445 |
| | antisense: 5'-UCCCGAACCAUCCGAACCUtt-3' | (136) | |
| siRNA-NM1 + 1 | sense: 5'-GUUCGGAUGGUUCGGGAACtt-3' | (137) | 481-499,429-447 |
| | antisense: 5'-GUUCCCGAACCAUCCGAACtt-3' | (138) | |

Vero cells were transfected with different doses of these siRNA, then infected with PPRV, RPV or MV as described in the section "Material and Methods".

3 to 5 days after infection, the production of the N, M and F proteins in the cells is measured by flow cytometry, as described in the section "Material and Methods".

The results obtained in nearly 70 experiments are illustrated in Table IV below.

TABLE IV

| Nature of siRNA (optimal concentration: | Inhibition of the expression of the nucleoprotein (in %) | | | Inhibition of the expression of the matrix protein (in %) | | | Inhibition of the expression of the fusion protein (in %) | | |
|---|---|---|---|---|---|---|---|---|---|
| 100 nM) | PPRV | RPV | MV | PPRV | RPV | MV | PPRV | RPV | MV |
| NPPR1 − 3 | 7 | nt | nt | nt | nt | nt | nt | nt | nt |
| NPPR1 − 2 | 15 | nt | nt | nt | nt | nt | nt | nt | nt |
| NPPR1 − 1 | 78 | 0 | 0 | 72 | nt | nt | nt | nt | nt |
| NPPR1 | 90 | 0 | 0 | 89 | 0 | nt | nt | nt | nt |
| NPPR1 + 1 | 24 | nt | nt | nt | nt | nt | nt | nt | nt |
| NPPR1 + 2 | 28 | nt | nt | nt | nt | nt | nt | nt | nt |
| NPPR6 − 2 | 12 | nt | nt | nt | nt | nt | nt | nt | nt |
| NPPR6 − 1 | 35 | nt | nt | nt | nt | nt | nt | nt | nt |
| NPPR6 | 80 | 4 | nt | 85 | nt | nt | nt | nt | nt |
| NPPR6 + 1 | 56 | nt | nt | nt | nt | nt | nt | nt | nt |
| NPPR6 + 2 | 41 | nt | nt | nt | nt | nt | nt | nt | nt |
| NPPR7 − 2 | 35 | nt | nt | nt | nt | nt | nt | nt | nt |
| NPPR7 − 1 | 44 | nt | nt | nt | nt | nt | nt | nt | nt |
| NPPR7 | 87 | 0 | nt | 83 | nt | nt | nt | nt | nt |
| NPPR7 + 1 | 62.5 | nt | nt | nt | nt | nt | nt | nt | nt |
| NPPR7 + 2 | 41 | nt | nt | nt | nt | nt | nt | nt | nt |
| NRP1 | 0 | 35 | 0 | nt | 31 | nt | nt | nt | nt |
| NRP1 + 1 | 0 | 97 | 0 | nt | 92 | nt | nt | nt | nt |
| NRP1 + 2 | 0 | 70 | 0 | nt | 80 | nt | nt | nt | nt |
| NRP1 + 3 | nt | 45 | nt | nt | nt | nt | nt | nt | nt |
| NRP6 − 2 | nt | 11 | nt | nt | nt | nt | nt | nt | nt |
| NRP6 − 1 | nt | 0 | nt | nt | nt | nt | nt | nt | nt |
| NRP6 (50 nM) | nt | 85 | nt | 5 | nt | nt | nt | 83 | nt |
| NRP6 + 1 | nt | 36 | nt | nt | nt | nt | nt | nt | nt |
| NRP6 + 2 | nt | 41 | nt | nt | nt | nt | nt | nt | nt |
| NRP7 − 2 | nt | 18 | nt | nt | nt | nt | nt | nt | nt |
| NRP7 − 1 | nt | 36 | nt | nt | nt | nt | nt | nt | nt |
| NRP7 | nt | 76.5 | nt | nt | nt | nt | nt | 81 | nt |
| NRP7 + 1 | nt | 85 | nt | 5 | nt | nt | nt | 86 | nt |
| NRP7 + 2 | nt | 49 | nt | nt | nt | nt | nt | nt | nt |
| NM1 − 2 | nt | nt | 35 | nt | nt | nt | nt | nt | nt |
| NM1 − 1 | nt | 0 | 85 | nt | nt | nt | nt | nt | nt |
| NM1 | 0 | 0 | 90 | nt | nt | nt | nt | nt | nt |
| NM1 + 1 | nt | nt | 28 | nt | nt | nt | nt | nt | nt |

nt: not tested.

The percentage inhibition of the production of the viral N protein induced by the transfection of the different siRNA into Vero cells is likewise illustrated in FIG. 6 (*a*) for the virus PPRV, (b) for the virus RPV and (c) for the virus MV. Inhibition of the expression of the N protein:

NPPRV:

A 90% inhibition of the expression of the N protein is observed with the siRNA NPPR1. This inhibition diminishes to 78%, 15% and 7% respectively with NPPR1−1, NPPR1−2 and NPPR1−3 and to less than 30% with NPPR1+T and NPPR1+2. Likewise, 80% inhibition is observed with the siRNA NPPR6, 56% inhibition with NPPR6+1 and 41% inhibition with NPPR6+2. The inhibition is 35% with NPPR6−1 and 70% with NPPR6−2. With NPPR7, 87% inhibition of the expression of the N protein is observed, and with NPPR7−1 and NPPR7−2 respectively 44% and 35% inhibition are observed. The percentage inhibition is 62.5% with NPPR7+1 and 41% with NPPR7+2. The results obtained with the siRNA-NPPR1 confirm those previously obtained in Example 3 (Table II). As regards the siRNAs NPPR6 and NPPR7, the results obtained from repeated experiments show that their efficacy is greater than that which had been evaluated in Example 3 from a single experiment.

NRPV:

A 35% inhibition of the expression of the N protein is observed with the siRNA NRP1 and 97% with NRP1+1. This inhibition diminishes to 70% and 45% respectively with NRP1+2 and NRP1+3.86% inhibition is observed with the siRNA NRP6. This inhibition diminishes to 11% with NRP6−2, and to 36% and 41% respectively with NRP6+1 and NRP6+2, and no inhibition is observed with NRP6−1. 76.5% inhibition of the expression of the N protein is observed with NRP7, and 36% and 18% inhibition respectively for NRP7−1 and NRP7−2. With NRP7+1, the percentage inhibition is 85%, and 49% for NRP7+2.

MV:

90% inhibition of the expression of the N protein is observed for NM1. This inhibition diminishes to 85%, and 35% respectively with NM1−1 and NM1−2 and to less than 30% with NM1+1.

Inhibition of the Expression of M Protein:

In PPRV, a decrease in expression by 72%, 89%, 85% and 83% respectively is observed with NPPR1−1, NPPR1, NPPR6 and NPPR7. In RPV, the decrease in expression is 31%, 92% and 80% respectively with NRP1, NRP1+1 and NRP1+2.

Inhibition of the Expression of F Protein:

In RPV, the inhibition of expression is 83%, 81% and 86% respectively with NRP6, NRP7 and NRP7+1.

These results show that the loci recognized by the siRNAs NPPR1, NPPR6, NPPR7, NRP1+1, NRP6 and NM1 constitute a particularly interesting and very precise target for the extinction of the N gene of morbillivirus. In the case of siRNA NRP7, the highest percentage inhibition is obtained for NRP7+1, hence the effective locus is shifted to 3' by one base. The measurement of the expression of the M and F proteins shows that the inhibition of the N protein also results in very strong inhibition of the other viral proteins.

The invention claimed is:

1. An isolated interfering RNA directed against a region of mRNA of the N gene encoding the nucleoprotein of a morbillivirus, said region containing a target motif which is selected from the group consisting of: GGUUCGGAUGGUUCGAGA (SEQ ID NO: 4) from the N gene of the measles virus; AGUCUUACUGGUUUGAGA (SEQ ID NO: 5) from the N gene of rinderpest virus (RPV); GAUCAACUGGUUUGAGA (SEQ ID NO: 6) from the N gene of small ruminants virus (PPRV); AAUUAGGCUGGUUAGAGA (SEQ ID NO: 7) from the N gene of Carré disease virus (CDV); AAAUGGGCUGGUUAGAAA (SEQ ID NO: 8) from the N gene of phocine distemper virus (PDV); and, GAACCCAUUGGUUUGAGA (SEQ ID NO: 9) from the N gene of dolphin morbillivirus (DMV).

2. The isolated interfering RNA as claimed in claim 1, wherein said interfering RNA comprises a 19 to 29 bp portion containing an antisense sequence of said target motif.

3. The isolated interfering RNA as claimed in claim 1 or 2, wherein said interfering RNA contains the following sequence:

in the case of the measles virus, UCUCGAACCAUCCGAACC (SEQ ID NO: 13);

in the case of RPV, UCUCAAACCAGUAAGACU (SEQ ID NO: 14);

in the case of PPRV, UCUCAAACCAGUUGAUCC (SEQ ID NO: 15);

in the case of CDV, UCUCUAACCAGCCUAAUU (SEQ ID NO: 16);

in the case of PDV, UUUCUAACCAGCCCAUUU (SEQ ID NO: 17); or in the case of DMV, UCUCAAACCAAUGGGUUC (SEQ ID NO: 18).

4. The isolated interfering RNA of claim 1, wherein the target motif is the nucleic acid sequence according to SEQ ID NO: 4.

5. The isolated interfering RNA of claim 1, wherein the target motif is the nucleic acid sequence according to SEQ ID NO: 5.

6. The isolated interfering RNA of claim 1, wherein the target motif is the nucleic acid sequence according to SEQ ID NO: 6.

7. The isolated interfering RNA of claim 1, wherein the target motif is the nucleic acid sequence according to SEQ ID NO: 7.

8. The isolated interfering RNA of claim 1, wherein the target motif is the nucleic acid sequence according to SEQ ID NO: 8.

9. The isolated interfering RNA of claim 1, wherein the target motif is the nucleic acid sequence according to SEQ ID NO: 9.

10. The isolated interfering RNA of claim 3, wherein the interfering RNA contains a nucleic acid sequence according to SEQ ID NO: 13.

11. The isolated interfering RNA of claim 3, wherein the interfering RNA contains a nucleic acid sequence according to SEQ ID NO: 14.

12. The isolated interfering RNA of claim 3, wherein the interfering RNA contains a nucleic acid sequence according to SEQ ID NO: 15.

13. The isolated interfering RNA of claim 3, wherein the interfering RNA contains a nucleic acid sequence according to SEQ ID NO: 16.

14. The isolated interfering RNA of claim 3, wherein the interfering RNA contains a nucleic acid sequence according to SEQ ID NO: 17.

15. The isolated interfering RNA of claim 3, wherein the interfering RNA contains a nucleic acid sequence according to SEQ ID NO: 18.

16. The isolated interfering RNA of claim 1, wherein the interfering RNA is selected from the siRNA, and shRNA.

17. An expression vector containing a DNA sequence capable of being transcribed into the isolated interfering RNA of claim 1, under control of an appropriate promoter.

18. The isolated interfering RNA of claim 1, further comprising a complementary sequence.

19. The isolated interfering RNA of claim 3, further comprising a complementary sequence.

* * * * *

SEQUENCE LISTING

```
<160> NUMBER OF SEQ ID NOS: 138

<210> SEQ ID NO 1
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: v= g, a or c ; r = a or g ; y = c or u ;
      w = a or u ; n = a, c, g or u
<220> FEATURE:
<221> NAME/KEY: misc_feature
<222> LOCATION: (5)..(6)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u

<400> SEQUENCE: 1

vrwynnrnug guungrra                                                18


<210> SEQ ID NO 2
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; w = a or u ;
      h = a, c or u ; n = a, c, g or u
<220> FEATURE:
<221> NAME/KEY: misc_feature
<222> LOCATION: (5)..(6)
<223> OTHER INFORMATION: n is a, c, g, or u

<400> SEQUENCE: 2

rrwynnrhug guuhgara                                                18


<210> SEQ ID NO 3
<211> LENGTH: 19
```

<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: v= g, a or c ; r = a or g ; y = c or u ;
w = a or u ; n = a, c, g or u
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 3
vvrwynnrnu gguungrra 19

<210> SEQ ID NO 4
<211> LENGTH: 18
<212> TYPE: RNA
<213> ORGANISM: Measles virus

<400> SEQUENCE: 4
gguucggaug guucgaga 18

<210> SEQ ID NO 5
<211> LENGTH: 18
<212> TYPE: RNA
<213> ORGANISM: Rinderpest virus

<400> SEQUENCE: 5
agucuuacug guuugaga 18

<210> SEQ ID NO 6
<211> LENGTH: 18
<212> TYPE: RNA
<213> ORGANISM: Small ruminants virus

<400> SEQUENCE: 6
ggaucaacug guuugaga 18

<210> SEQ ID NO 7
<211> LENGTH: 18
<212> TYPE: RNA
<213> ORGANISM: canine distemper virus

<400> SEQUENCE: 7
aauuaggcug guuagaga 18

<210> SEQ ID NO 8
<211> LENGTH: 18
<212> TYPE: RNA
<213> ORGANISM: Phocine distemper virus

<400> SEQUENCE: 8
aaaugggcug guuagaaa 18

<210> SEQ ID NO 9
<211> LENGTH: 18
<212> TYPE: RNA
<213> ORGANISM: Dolphin morbillivirus

<400> SEQUENCE: 9
gaacccauug guuugaga 18

<210> SEQ ID NO 10
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; w = a or u ;
b = g, u or c ; n = a, c, g or u
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (13)..(14)
<223> OTHER INFORMATION: n is a, c, g, or u

<400> SEQUENCE: 10
uyycnaacca nynnrwyb 18

<210> SEQ ID NO 11
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; w = a or u ;
d = a, g or u ; h = a, c or u ; n = a, c, g or u
<220> FEATURE:
<221> NAME/KEY: misc_feature
<222> LOCATION: (13)..(14)
<223> OTHER INFORMATION: n is a, c, g, or u

<400> SEQUENCE: 11
uyucdaacca dynnrwyy 18

<210> SEQ ID NO 12
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; w = a or u ;
b = g, u or c ; n = a, c, g or u
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (13)..(14)
<223> OTHER INFORMATION: n is a, c, g, or u

<400> SEQUENCE: 12
uyycnaacca nynnrwybb 19

<210> SEQ ID NO 13
<211> LENGTH: 18
<212> TYPE: RNA
<213> ORGANISM: Measles virus

<400> SEQUENCE: 13
ucucgaacca uccgaacc                                                 18

<210> SEQ ID NO 14
<211> LENGTH: 18
<212> TYPE: RNA
<213> ORGANISM: Rinderpest virus

<400> SEQUENCE: 14
ucucaaacca guaagacu                                                 18

<210> SEQ ID NO 15
<211> LENGTH: 18
<212> TYPE: RNA
<213> ORGANISM: Small ruminants virus

<400> SEQUENCE: 15
ucucaaacca guugaucc                                                 18

<210> SEQ ID NO 16
<211> LENGTH: 18
<212> TYPE: RNA
<213> ORGANISM: canine distemper virus

<400> SEQUENCE: 16
ucucuaacca gccuaauu                                                 18

<210> SEQ ID NO 17
<211> LENGTH: 18
<212> TYPE: RNA
<213> ORGANISM: Phocine distemper virus

<400> SEQUENCE: 17
uuucuaacca gcccauuu                                                 18

<210> SEQ ID NO 18
<211> LENGTH: 18
<212> TYPE: RNA
<213> ORGANISM: Dolphin morbillivirus

<400> SEQUENCE: 18
ucucaaacca auggguuc                                                 18

<210> SEQ ID NO 19
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; m = a or c ;
      k = g or u ; n = a, c, g or u ; w = a or u
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u

```
<220> FEATURE:
<221> NAME/KEY: misc_feature
<222> LOCATION: (17)..(17)
<223> OTHER INFORMATION: n is a, c, g, or u

<400> SEQUENCE: 19

gnmkruuywu ggunkcnyu                                               19


<210> SEQ ID NO 20
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; m = a or c ;
      d = a, g or u ; v = g, a or c ; k = g or u ; s = g or c

<400> SEQUENCE: 20

gsmgruuyau gguvkcdyu                                               19


<210> SEQ ID NO 21
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; h = a, c or u ;
      d = a, g or u ; n = a, c, g or u ; s = g or c
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u

<400> SEQUENCE: 21

chyungsnyu dcaygaru                                                18


<210> SEQ ID NO 22
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; h = a, c or u ;
      d = a, g or u ; n = a, c, g or u ; s = g or c
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u

<400> SEQUENCE: 22

chyungsnyu dcaygaruu                                               19


<210> SEQ ID NO 23
<211> LENGTH: 19
<212> TYPE: RNA
<213> ORGANISM: Artificial sequence
<220> FEATURE:
<223> OTHER INFORMATION: Consensus sequence
```

<220> FEATURE:
<221> NAME/KEY: misc_feature
<223> OTHER INFORMATION: r = a or g ; y = c or u ; h = a, c or u ;
d = a, g or u ; n = a, c, g or u ; s = g or c
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u

<400> SEQUENCE: 23
gchyungsny udcaygaru 19

<210> SEQ ID NO 24
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; h = a, c or u ;
d = a, g or u ; n = a, c, g or u
<220> FEATURE:
<221> NAME/KEY: misc_feature
<222> LOCATION: (9)..(9)
<223> OTHER INFORMATION: n is a, c, g, or u

<400> SEQUENCE: 24
gchyudggny udcaygaru 19

<210> SEQ ID NO 25
<211> LENGTH: 19
<212> TYPE: RNA
<213> ORGANISM: Measles virus

<400> SEQUENCE: 25
gccgauucau ggucgcucu 19

<210> SEQ ID NO 26
<211> LENGTH: 19
<212> TYPE: RNA
<213> ORGANISM: Measles virus

<400> SEQUENCE: 26
gcucuuggac ugcaugaau 19

<210> SEQ ID NO 27
<211> LENGTH: 19
<212> TYPE: RNA
<213> ORGANISM: Rinderpest virus

<400> SEQUENCE: 27
gcagauuuau gguggcauu 19

<210> SEQ ID NO 28
<211> LENGTH: 19
<212> TYPE: RNA
<213> ORGANISM: Rinderpest virus

<400> SEQUENCE: 28
gcacugggcc ugcaugaau 19

<210> SEQ ID NO 29
<211> LENGTH: 19

-continued

<212> TYPE: RNA
<213> ORGANISM: Small ruminants virus

<400> SEQUENCE: 29
ggcgguucau gguaucucu 19

<210> SEQ ID NO 30
<211> LENGTH: 19
<212> TYPE: RNA
<213> ORGANISM: Small ruminants virus

<400> SEQUENCE: 30
gcauuaggcc uucacgagu 19

<210> SEQ ID NO 31
<211> LENGTH: 19
<212> TYPE: RNA
<213> ORGANISM: canine distemper virus

<400> SEQUENCE: 31
ggcgauucau gguggcgcu 19

<210> SEQ ID NO 32
<211> LENGTH: 19
<212> TYPE: RNA
<213> ORGANISM: canine distemper virus

<400> SEQUENCE: 32
gcucuugggu ugcaugagu 19

<210> SEQ ID NO 33
<211> LENGTH: 19
<212> TYPE: RNA
<213> ORGANISM: Phocine distemper virus

<400> SEQUENCE: 33
ggcgauuuau gguggcauu 19

<210> SEQ ID NO 34
<211> LENGTH: 19
<212> TYPE: RNA
<213> ORGANISM: Phocine distemper virus

<400> SEQUENCE: 34
gcacuugguc uacaugagu 19

<210> SEQ ID NO 35
<211> LENGTH: 19
<212> TYPE: RNA
<213> ORGANISM: Dolphin morbillivirus

<400> SEQUENCE: 35
ggagauucau gguggcauu 19

<210> SEQ ID NO 36
<211> LENGTH: 19
<212> TYPE: RNA
<213> ORGANISM: Dolphin morbillivirus

<400> SEQUENCE: 36
gccuuagggu ugcaugaau 19

<210> SEQ ID NO 37
<211> LENGTH: 19

<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; m = a or c ;
k = g or u ; s = g or c ; w = a or u ; n = a, c, g or u
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u

<400> SEQUENCE: 37
arngmnacca wraaymknc 19

<210> SEQ ID NO 38
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; m = a or c ; b = g,
u or c ; h = a, c or u ; k = g or u ; s = g or c

<400> SEQUENCE: 38
arhgmbacca uraaycksc 19

<210> SEQ ID NO 39
<211> LENGTH: 18
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; d = g, a or u ;
n = a, c, g or u ; s = g or c
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u

<400> SEQUENCE: 39
ayucrughar nscnardg 18

<210> SEQ ID NO 40
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; d = g, a or u ;
n = a, c, g or u ; s = g or c
<220> FEATURE:
<221> NAME/KEY: misc_feature
<222> LOCATION: (12)..(12)
<223> OTHER INFORMATION: n is a, c, g, or u -continued
<220> FEATURE:
<221> NAME/KEY: misc_feature
<222> LOCATION: (15)..(15)
<223> OTHER INFORMATION: n is a, c, g, or u

<400> SEQUENCE: 40
aayucrugha rnscnardg 19

<210> SEQ ID NO 41
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; d = g, a or u ;
n = a, c, g or u ; s = g or c
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u

<400> SEQUENCE: 41
ayucrughar nscnardgc 19

<210> SEQ ID NO 42
<211> LENGTH: 19
<212> TYPE: RNA
<213> ORGANISM: Artificial sequence
<220> FEATURE:
<223> OTHER INFORMATION: Consensus sequence
<220> FEATURE:
<221> NAME/KEY: misc_feature
<223> OTHER INFORMATION: r = a or g ; y = c or u ; d = g, a or u ;
h = a, c or u ; n = a, c, g or u
<220> FEATURE:
<221> NAME/KEY: misc_feature
<222> LOCATION: (11)..(11)
<223> OTHER INFORMATION: n is a, c, g, or u

<400> SEQUENCE: 42
ayucrughar ncchardgc 19

<210> SEQ ID NO 43
<211> LENGTH: 19
<212> TYPE: RNA
<213> ORGANISM: Measles virus

<400> SEQUENCE: 43
agagcgacca ugaaucggc 19

<210> SEQ ID NO 44
<211> LENGTH: 19
<212> TYPE: RNA
<213> ORGANISM: Rinderpest virus

<400> SEQUENCE: 44
aaugccacca uaaaucugc 19

<210> SEQ ID NO 45
<211> LENGTH: 19
<212> TYPE: RNA
<213> ORGANISM: Small ruminants virus

<400> SEQUENCE: 45

-continued agagauacca ugaaccgcc 19

<210> SEQ ID NO 46
<211> LENGTH: 19
<212> TYPE: RNA
<213> ORGANISM: canine distemper virus

<400> SEQUENCE: 46
agcgccacca ugaaucgcc 19

<210> SEQ ID NO 47
<211> LENGTH: 19
<212> TYPE: RNA
<213> ORGANISM: Phocine distemper virus

<400> SEQUENCE: 47
aaugccacca uaaaucgcc 19

<210> SEQ ID NO 48
<211> LENGTH: 19
<212> TYPE: DNA
<213> ORGANISM: Dolphin morbillivirus

<400> SEQUENCE: 48
aaugccacca ugaaucucc 19

<210> SEQ ID NO 49
<211> LENGTH: 19
<212> TYPE: RNA
<213> ORGANISM: Measles virus

<400> SEQUENCE: 49
auucaugcag uccaagagc 19

<210> SEQ ID NO 50
<211> LENGTH: 19
<212> TYPE: RNA
<213> ORGANISM: Rinderpest virus

<400> SEQUENCE: 50
auucaugcag gcccagugc 19

<210> SEQ ID NO 51
<211> LENGTH: 19
<212> TYPE: RNA
<213> ORGANISM: Small ruminants virus

<400> SEQUENCE: 51
acucgugaag gccuaaugc 19

<210> SEQ ID NO 52
<211> LENGTH: 19
<212> TYPE: RNA
<213> ORGANISM: canine distemper virus

<400> SEQUENCE: 52
acucaugcaa cccaagagc 19

<210> SEQ ID NO 53
<211> LENGTH: 19
<212> TYPE: RNA
<213> ORGANISM: Phocine distemper virus

<400> SEQUENCE: 53
acucauguag accaagugc 19

<210> SEQ ID NO 54
<211> LENGTH: 19
<212> TYPE: DNA
<213> ORGANISM: Dolphin morbillivirus

<400> SEQUENCE: 54
auucaugcaa cccuaaggc 19

<210> SEQ ID NO 55
<211> LENGTH: 21
<212> TYPE: DNA
<213> ORGANISM: Artificial sequence
<220> FEATURE:
<223> OTHER INFORMATION: PCR Primer

<400> SEQUENCE: 55
gtctcggaaa tcgcctcaca g 21

<210> SEQ ID NO 56
<211> LENGTH: 21
<212> TYPE: DNA
<213> ORGANISM: Artificial sequence
<220> FEATURE:
<223> OTHER INFORMATION: PCR Primer

<400> SEQUENCE: 56
cctcctcctg gtcctccaga a 21

<210> SEQ ID NO 57
<211> LENGTH: 21
<212> TYPE: DNA
<213> ORGANISM: Small ruminants virus

<400> SEQUENCE: 57
ggaucaacug guuugagaat t 21

<210> SEQ ID NO 58
<211> LENGTH: 21
<212> TYPE: DNA
<213> ORGANISM: Small ruminants virus

<400> SEQUENCE: 58
uucucaaacc aguugaucct t 21

<210> SEQ ID NO 59
<211> LENGTH: 21
<212> TYPE: DNA
<213> ORGANISM: Small ruminants virus

<400> SEQUENCE: 59
gcucaccuuc auucuuuuct t 21

<210> SEQ ID NO 60
<211> LENGTH: 21
<212> TYPE: DNA
<213> ORGANISM: Small ruminants virus

<400> SEQUENCE: 60
gaaaagaaug aaggugagct c 21

<210> SEQ ID NO 61
<211> LENGTH: 21

<212> TYPE: DNA
<213> ORGANISM: Small ruminants virus

<400> SEQUENCE: 61
ggccaguuuc auucuuacut t 21

<210> SEQ ID NO 62
<211> LENGTH: 21
<212> TYPE: DNA
<213> ORGANISM: Small ruminants virus

<400> SEQUENCE: 62
aguaagaaug aaacuggcct c 21

<210> SEQ ID NO 63
<211> LENGTH: 21
<212> TYPE: DNA
<213> ORGANISM: Small ruminants virus

<400> SEQUENCE: 63
gagaacucaa uucagaacat t 21

<210> SEQ ID NO 64
<211> LENGTH: 21
<212> TYPE: DNA
<213> ORGANISM: Small ruminants virus

<400> SEQUENCE: 64
uguucugaau ugaguucuct t 21

<210> SEQ ID NO 65
<211> LENGTH: 21
<212> TYPE: DNA
<213> ORGANISM: Small ruminants virus

<400> SEQUENCE: 65
ggcgguucau gguaucucut t 21

<210> SEQ ID NO 66
<211> LENGTH: 21
<212> TYPE: DNA
<213> ORGANISM: Small ruminants virus

<400> SEQUENCE: 66
agagauacca ugaaccgcct t 21

<210> SEQ ID NO 67
<211> LENGTH: 21
<212> TYPE: DNA
<213> ORGANISM: Small ruminants virus

<400> SEQUENCE: 67
gcauuaggcc uucacgagut t 21

<210> SEQ ID NO 68
<211> LENGTH: 21
<212> TYPE: DNA
<213> ORGANISM: Small ruminants virus

<400> SEQUENCE: 68
acucgugaag gccuaaugct t 21

<210> SEQ ID NO 69
<211> LENGTH: 21

<212> TYPE: DNA
<213> ORGANISM: Small ruminants virus

<400> SEQUENCE: 69
guaucaacag cuaggagagt t 21

<210> SEQ ID NO 70
<211> LENGTH: 21
<212> TYPE: DNA
<213> ORGANISM: Small ruminants virus

<400> SEQUENCE: 70
cucuccuagc uguugauact t 21

<210> SEQ ID NO 71
<211> LENGTH: 21
<212> TYPE: DNA
<213> ORGANISM: Small ruminants virus

<400> SEQUENCE: 71
gaacuuuggc aggucauaut t 21

<210> SEQ ID NO 72
<211> LENGTH: 21
<212> TYPE: DNA
<213> ORGANISM: Small ruminants virus

<400> SEQUENCE: 72
auaugaccug ccaaaguuct t 21

<210> SEQ ID NO 73
<211> LENGTH: 21
<212> TYPE: DNA
<213> ORGANISM: Small ruminants virus

<400> SEQUENCE: 73
cgccaguuuc auucuuacut t 21

<210> SEQ ID NO 74
<211> LENGTH: 21
<212> TYPE: DNA
<213> ORGANISM: Small ruminants virus

<400> SEQUENCE: 74
aguaagaaug aaacuggcgt t 21

<210> SEQ ID NO 75
<211> LENGTH: 21
<212> TYPE: DNA
<213> ORGANISM: Rinderpest virus

<400> SEQUENCE: 75
gcagucuuac ugguuugagt t 21

<210> SEQ ID NO 76
<211> LENGTH: 21
<212> TYPE: DNA
<213> ORGANISM: Rinderpest virus

<400> SEQUENCE: 76
cucaaaccag uaagacugct t 21

<210> SEQ ID NO 77
<211> LENGTH: 21

```
<212> TYPE: DNA
<213> ORGANISM: Rinderpest virus

<400> SEQUENCE: 77

cagucuuacu gguuugagat t                                              21


<210> SEQ ID NO 78
<211> LENGTH: 21
<212> TYPE: DNA
<213> ORGANISM: Rinderpest virus

<400> SEQUENCE: 78

ucucaaacca guaagacugt c                                              21


<210> SEQ ID NO 79
<211> LENGTH: 21
<212> TYPE: DNA
<213> ORGANISM: Rinderpest virus

<400> SEQUENCE: 79

gcagauuuau gguggcauut t                                              21


<210> SEQ ID NO 80
<211> LENGTH: 21
<212> TYPE: DNA
<213> ORGANISM: Rinderpest virus

<400> SEQUENCE: 80

aaugccacca uaaaucugct t                                              21


<210> SEQ ID NO 81
<211> LENGTH: 21
<212> TYPE: DNA
<213> ORGANISM: Rinderpest virus

<400> SEQUENCE: 81

gcacugggcc ugcaugaaut t                                              21


<210> SEQ ID NO 82
<211> LENGTH: 21
<212> TYPE: DNA
<213> ORGANISM: Rinderpest virus

<400> SEQUENCE: 82

auucaugcag gcccagugct t                                              21


<210> SEQ ID NO 83
<211> LENGTH: 21
<212> TYPE: DNA
<213> ORGANISM: Measles virus

<400> SEQUENCE: 83

gguucggaug guucgggaat t                                              21


<210> SEQ ID NO 84
<211> LENGTH: 21
<212> TYPE: DNA
<213> ORGANISM: Measles virus

<400> SEQUENCE: 84

uucccgaacc auccgaacct t                                              21


<210> SEQ ID NO 85
<211> LENGTH: 21
```

<212> TYPE: DNA
<213> ORGANISM: Artificial sequence
<220> FEATURE:
<223> OTHER INFORMATION: Sense siRNA-GAPDH

<400> SEQUENCE: 85
aaggucaucc augacaacut t 21

<210> SEQ ID NO 86
<211> LENGTH: 21
<212> TYPE: DNA
<213> ORGANISM: Artificial sequence
<220> FEATURE:
<223> OTHER INFORMATION: Antisense siRNA-GAPDH

<400> SEQUENCE: 86
aguugucaug gaugaccuut t 21

<210> SEQ ID NO 87
<211> LENGTH: 21
<212> TYPE: DNA
<213> ORGANISM: Small ruminants virus

<400> SEQUENCE: 87
aaaggaucaa cugguuugat t 21

<210> SEQ ID NO 88
<211> LENGTH: 21
<212> TYPE: DNA
<213> ORGANISM: Small ruminants virus

<400> SEQUENCE: 88
ucaaaccagu ugauccuuut c 21

<210> SEQ ID NO 89
<211> LENGTH: 21
<212> TYPE: DNA
<213> ORGANISM: Small ruminants virus

<400> SEQUENCE: 89
aaggaucaac ugguuugagt t 21

<210> SEQ ID NO 90
<211> LENGTH: 21
<212> TYPE: DNA
<213> ORGANISM: Small ruminants virus

<400> SEQUENCE: 90
cucaaaccag uugauccuut t 21

<210> SEQ ID NO 91
<211> LENGTH: 21
<212> TYPE: DNA
<213> ORGANISM: Small ruminants virus

<400> SEQUENCE: 91
aggaucaacu gguuugagat t 21

<210> SEQ ID NO 92
<211> LENGTH: 21
<212> TYPE: DNA
<213> ORGANISM: Small ruminants virus

<400> SEQUENCE: 92
ucucaaacca guugauccut t 21

<210> SEQ ID NO 93
<211> LENGTH: 21
<212> TYPE: DNA
<213> ORGANISM: Small ruminants virus

<400> SEQUENCE: 93
gaucaacugg uuugagaact t 21

<210> SEQ ID NO 94
<211> LENGTH: 21
<212> TYPE: DNA
<213> ORGANISM: Small ruminants virus

<400> SEQUENCE: 94
guucucaaac caguugauct t 21

<210> SEQ ID NO 95
<211> LENGTH: 21
<212> TYPE: DNA
<213> ORGANISM: Small ruminants virus

<400> SEQUENCE: 95
aucaacuggu uugagaacat t 21

<210> SEQ ID NO 96
<211> LENGTH: 21
<212> TYPE: DNA
<213> ORGANISM: Small ruminants virus

<400> SEQUENCE: 96
uguucucaaa ccaguugaut c 21

<210> SEQ ID NO 97
<211> LENGTH: 21
<212> TYPE: DNA
<213> ORGANISM: Small ruminants virus

<400> SEQUENCE: 97
ucggcgguuc augguaucut t 21

<210> SEQ ID NO 98
<211> LENGTH: 21
<212> TYPE: DNA
<213> ORGANISM: Small ruminants virus

<400> SEQUENCE: 98
agauaccaug aaccgccgat t 21

<210> SEQ ID NO 99
<211> LENGTH: 21
<212> TYPE: DNA
<213> ORGANISM: Small ruminants virus

<400> SEQUENCE: 99
cggcgguuca ugguaucuct t 21

<210> SEQ ID NO 100
<211> LENGTH: 21
<212> TYPE: DNA
<213> ORGANISM: Small ruminants virus

<400> SEQUENCE: 100
gagauaccau gaaccgccgt t 21

<210> SEQ ID NO 101
<211> LENGTH: 21
<212> TYPE: DNA
<213> ORGANISM: Small ruminants virus

<400> SEQUENCE: 101
gcgguucaug guaucucuct t 21

<210> SEQ ID NO 102
<211> LENGTH: 21
<212> TYPE: DNA
<213> ORGANISM: Small ruminants virus

<400> SEQUENCE: 102
gagagauacc augaaccgct t 21

<210> SEQ ID NO 103
<211> LENGTH: 21
<212> TYPE: DNA
<213> ORGANISM: Small ruminants virus

<400> SEQUENCE: 103
cgguucaugg uaucucucat t 21

<210> SEQ ID NO 104
<211> LENGTH: 21
<212> TYPE: DNA
<213> ORGANISM: Small ruminants virus

<400> SEQUENCE: 104
ugagagauac caugaaccgt t 21

<210> SEQ ID NO 105
<211> LENGTH: 21
<212> TYPE: DNA
<213> ORGANISM: Small ruminants virus

<400> SEQUENCE: 105
cugcauuagg ccuucacgat t 21

<210> SEQ ID NO 106
<211> LENGTH: 21
<212> TYPE: DNA
<213> ORGANISM: Small ruminants virus

<400> SEQUENCE: 106
ucgugaaggc cuaaugcagt t 21

<210> SEQ ID NO 107
<211> LENGTH: 21
<212> TYPE: DNA
<213> ORGANISM: Small ruminants virus

<400> SEQUENCE: 107
ugcauuaggc cuucacgagt t 21

<210> SEQ ID NO 108
<211> LENGTH: 21
<212> TYPE: DNA
<213> ORGANISM: Small ruminants virus

<400> SEQUENCE: 108
cucgugaagg ccuaaugcat t 21

-continued

<210> SEQ ID NO 109
<211> LENGTH: 21
<212> TYPE: DNA
<213> ORGANISM: Small ruminants virus

<400> SEQUENCE: 109
cauuaggccu ucacgaguut t 21

<210> SEQ ID NO 110
<211> LENGTH: 21
<212> TYPE: DNA
<213> ORGANISM: Small ruminants virus

<400> SEQUENCE: 110
aacucgugaa ggccuaaugt t 21

<210> SEQ ID NO 111
<211> LENGTH: 21
<212> TYPE: DNA
<213> ORGANISM: Small ruminants virus

<400> SEQUENCE: 111
auuaggccuu cacgaguugt t 21

<210> SEQ ID NO 112
<211> LENGTH: 21
<212> TYPE: DNA
<213> ORGANISM: Small ruminants virus

<400> SEQUENCE: 112
caacucguga aggccuaaut t 21

<210> SEQ ID NO 113
<211> LENGTH: 21
<212> TYPE: DNA
<213> ORGANISM: Rinderpest virus

<400> SEQUENCE: 113
acgcagauuu augguggcat t 21

<210> SEQ ID NO 114
<211> LENGTH: 21
<212> TYPE: DNA
<213> ORGANISM: Rinderpest virus

<400> SEQUENCE: 114
ugccaccaua aaucugcgut t 21

<210> SEQ ID NO 115
<211> LENGTH: 21
<212> TYPE: DNA
<213> ORGANISM: Rinderpest virus

<400> SEQUENCE: 115
cgcagauuua ugguggcaut t 21

<210> SEQ ID NO 116
<211> LENGTH: 21
<212> TYPE: DNA
<213> ORGANISM: Rinderpest virus

<400> SEQUENCE: 116
augccaccau aaaucugcgt t 21

<210> SEQ ID NO 117
<211> LENGTH: 21
<212> TYPE: DNA
<213> ORGANISM: Rinderpest virus

<400> SEQUENCE: 117
cagauuuaug guggcauugt t 21

<210> SEQ ID NO 118
<211> LENGTH: 21
<212> TYPE: DNA
<213> ORGANISM: Rinderpest virus

<400> SEQUENCE: 118
caaugccacc auaaaucugt t 21

<210> SEQ ID NO 119
<211> LENGTH: 21
<212> TYPE: DNA
<213> ORGANISM: Rinderpest virus

<400> SEQUENCE: 119
agauuuaugg uggcauugat t 21

<210> SEQ ID NO 120
<211> LENGTH: 21
<212> TYPE: DNA
<213> ORGANISM: Rinderpest virus

<400> SEQUENCE: 120
ucaaugccac cauaaaucut t 21

<210> SEQ ID NO 121
<211> LENGTH: 21
<212> TYPE: DNA
<213> ORGANISM: Rinderpest virus

<400> SEQUENCE: 121
cagcacuggg ccugcaugat t 21

<210> SEQ ID NO 122
<211> LENGTH: 21
<212> TYPE: DNA
<213> ORGANISM: Rinderpest virus

<400> SEQUENCE: 122
ucaugcaggc ccagugcuct t 21

<210> SEQ ID NO 123
<211> LENGTH: 21
<212> TYPE: DNA
<213> ORGANISM: Rinderpest virus

<400> SEQUENCE: 123
agcacugggc cugcaugaat t 21

<210> SEQ ID NO 124
<211> LENGTH: 21
<212> TYPE: DNA
<213> ORGANISM: Rinderpest virus

<400> SEQUENCE: 124
uucaugcagg cccagugcut t 21

<210> SEQ ID NO 125
<211> LENGTH: 21
<212> TYPE: DNA
<213> ORGANISM: Rinderpest virus

<400> SEQUENCE: 125
cacugggccu gcaugaauut t 21

<210> SEQ ID NO 126
<211> LENGTH: 21
<212> TYPE: DNA
<213> ORGANISM: Rinderpest virus

<400> SEQUENCE: 126
aauucaugca ggcccagugt t 21

<210> SEQ ID NO 127
<211> LENGTH: 21
<212> TYPE: DNA
<213> ORGANISM: Rinderpest virus

<400> SEQUENCE: 127
acugggccug caugaauuct t 21

<210> SEQ ID NO 128
<211> LENGTH: 21
<212> TYPE: DNA
<213> ORGANISM: Rinderpest virus

<400> SEQUENCE: 128
gaauucaugc aggcccagut t 21

<210> SEQ ID NO 129
<211> LENGTH: 21
<212> TYPE: DNA
<213> ORGANISM: Rinderpest virus

<400> SEQUENCE: 129
agucuuacug guuugagaat t 21

<210> SEQ ID NO 130
<211> LENGTH: 21
<212> TYPE: DNA
<213> ORGANISM: Rinderpest virus

<400> SEQUENCE: 130
uucucaaacc aguaagacut c 21

<210> SEQ ID NO 131
<211> LENGTH: 21
<212> TYPE: DNA
<213> ORGANISM: Rinderpest virus

<400> SEQUENCE: 131
gucuuacugg uuugagaaut t 21

<210> SEQ ID NO 132
<211> LENGTH: 21
<212> TYPE: DNA
<213> ORGANISM: Rinderpest virus

<400> SEQUENCE: 132
cccgaaccau ccgaaccugt t 21

-continued

<210> SEQ ID NO 133
<211> LENGTH: 21
<212> TYPE: DNA
<213> ORGANISM: Measles virus

<400> SEQUENCE: 133
cagguucgga ugguucgggt t 21

<210> SEQ ID NO 134
<211> LENGTH: 21
<212> TYPE: DNA
<213> ORGANISM: Measles virus

<400> SEQUENCE: 134
uucucaaacc aguaagacut c 21

<210> SEQ ID NO 135
<211> LENGTH: 21
<212> TYPE: DNA
<213> ORGANISM: Measles virus

<400> SEQUENCE: 135
agguucggau gguucgggat t 21

<210> SEQ ID NO 136
<211> LENGTH: 21
<212> TYPE: DNA
<213> ORGANISM: Measles virus

<400> SEQUENCE: 136
ucccgaacca uccgaaccut t 21

<210> SEQ ID NO 137
<211> LENGTH: 21
<212> TYPE: DNA
<213> ORGANISM: Measles virus

<400> SEQUENCE: 137
guucggaugg uucgggaact t 21

<210> SEQ ID NO 138
<211> LENGTH: 21
<212> TYPE: DNA
<213> ORGANISM: Measles virus

<400> SEQUENCE: 138
guucccgaac cauccgaact t 21